US010266603B2

(12) United States Patent
McMullen et al.

(10) Patent No.: US 10,266,603 B2
(45) Date of Patent: Apr. 23, 2019

(54) TARGETED THERAPY TO RESTORE RADIOACTIVE IODINE TRANSPORT IN THYROID CANCER

(71) Applicant: The Governors of the University of Alberta, Edmonton (CA)

(72) Inventors: Todd McMullen, Edmonton (CA); Ana Lopez-Campistrous, Edmonton (CA); David Williams, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 15/304,394

(22) PCT Filed: Apr. 17, 2015

(86) PCT No.: PCT/IB2015/001426
§ 371 (c)(1),
(2) Date: Oct. 14, 2016

(87) PCT Pub. No.: WO2015/166355
PCT Pub. Date: Nov. 5, 2015

(65) Prior Publication Data
US 2017/0037143 A1 Feb. 9, 2017

Related U.S. Application Data

(60) Provisional application No. 61/981,358, filed on Apr. 18, 2014.

(51) Int. Cl.
| | |
|---|---|
| *C07K 16/30* | (2006.01) |
| *C07K 16/28* | (2006.01) |
| *A61K 45/06* | (2006.01) |
| *A61K 51/00* | (2006.01) |
| *C07K 14/71* | (2006.01) |
| *A61K 39/395* | (2006.01) |
| *A61K 31/7088* | (2006.01) |
| *C12N 15/113* | (2010.01) |
| *G01N 33/68* | (2006.01) |

(52) U.S. Cl.
CPC .......... *C07K 16/30* (2013.01); *A61K 31/7088* (2013.01); *A61K 39/39558* (2013.01); *A61K 45/06* (2013.01); *A61K 51/00* (2013.01); *C07K 14/71* (2013.01); *C07K 16/28* (2013.01); *C12N 15/1138* (2013.01); *G01N 33/6872* (2013.01); *C07K 2317/76* (2013.01); *C12N 2310/14* (2013.01); *C12N 2320/31* (2013.01); *C12N 2320/32* (2013.01); *G01N 2333/4703* (2013.01); *G01N 2333/71* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortz Man | |
| 4,938,949 A | 7/1990 | Borch et al. | |
| 4,992,478 A | 2/1991 | Geria | |
| 2015/0010582 A1* | 1/2015 | Mcmullen | G01N 33/57407 424/174.1 |

FOREIGN PATENT DOCUMENTS

| | | |
|---|---|---|
| WO | WO-2007/044515 A1 | 4/2007 |
| WO | WO-2013/113102 A1 | 8/2013 |

OTHER PUBLICATIONS

Aparicio-Gallego et al., New insights into molecular mechanism of Sunitinib-associated side effects. Mol. Cancer Ther. 10, 2215-2223, 2011.*
NIH Clinical Trial NCT01321554 (first published Mar. 23, 2011) retrieved at https://clinicaltrials.gov/ct2/home.*
Tohyama et al. J. Thyroid Res. vol. 2014, Article ID 638747, 13 pages.*
NIH clinical trial NCT01229644-posted Oct. 28, 2010 retrieved at https://clinicaltrials.gov/ct2/home.*
Nicolaou et al., "Calicheamicin theta: A Rationally Designed Molecule with Extremely Potent and Selective DNA Cleaving Properties and Apoptosis Inducing Activity," Angew Chem Int Ed Engl. 33(2): 183-6 (1994).
Castagna et al., "Limited Value of repeat recombinant human thyrotropin (rhTSH)-Stimulated Thyroglobulin Testing in Differentiated Thryoid Carcinoma Patients with Previous Negative rhTSH-Stimulated Thyroglobulin and Undetectable Basal Serum Thyroglobulin Levels," J Clin Endocrinol Metab. 93 (1): 76-81 (2008).
Coleman et al., Effectors of Humoral Immunity. Fundamental Immunology. 2nd Edition, 55-73 (1989).
Cooper et al., "Management Guidelines for Patients with Thyroid Nodules and Differentiated Thyroid Cancer", Thyroid. 16(2): 109-148 (2006).
Ho et al., "Selumetinib-Enhanced Radioiodine Uptake in Advanced Thyroid Cancer," N. Engl J Med. 368(7): 623-32 (2013).
How et al., "Explaining the Increasing Incidence of Differentiated Thyroid Cancer," CMAJ. 177(11): 1383-84 (2007).
Loizos et al., "Targeting the Platelet-Derived Growth Factor Receptor Alpha with a Neutralizing Human Monoclonal Antibody Inhibits the Growth of Tumor Xenografts: Implications as a Potential Therapeutic Target," Mol Cancer Ther. 4(3):369-79 (2005).
Mu et al., "Combining Transfer of TTF-1 and Pax-8 gene: a Potential Strategy to Promote Radioiodine Therapy of Thyroid Carcinoma," Cancer Gene Ther. 19 (6): 402-11 (2012).

(Continued)

*Primary Examiner* — Elly-Gerald Stoica
(74) *Attorney, Agent, or Firm* — Clark & Elbing LLP

(57) ABSTRACT

The invention includes method, pharmaceutical compositions and uses thereof for treating patients with Papillary Thyroid Carcinoma (PTC) using a Platelet Derived Growth Factor Receptor Alpha (PDGFRA) inhibitor. The PDGFRA inhibitor is preferably an antibody specific to PDGFRA and causes an increase in the sensitivity level of PTC cells to radioiodine treatment. Moreover, the antibody can be used in combination with other PDGFRA inhibitors such as tyrosine kinase inhibitors and RNA interference molecules.

13 Claims, 14 Drawing Sheets

(56) References Cited

OTHER PUBLICATIONS

Rotstein, "The Role of Lymphadenectomy in the Management of Papillary Carcinoma of the Thyroid", J Surg Oncol. 99(4): 186-88 (2009).
Sakorafas et al., "Cervical lymph Node Dissection in Papillary Thyroid Cancer: Current Trends, Persisting Controversies, and Unclarified Uncertainties," Surg Oncol. 19(2): e57-e70 (2010).
Verbeek et al., "The Effects of Four Different Tyrosine Kinase Inhibitors on Medullary and Papillary Thyroid Cancer Cells," J Clin Endocrinol Metab. 96(6): E991-E995 (2011).
Zhang et al., "Platelet-Derived Growth Factor Receptor-Alpha Promotes Lymphatic Metastases in Papillary Thyroid Cancer," J Pathol. 228 (2): 241-50 (2012).
International Search Report for International Application No. PCT/IB2015/001426, dated Nov. 19, 2015 (5 pages).
International Preliminary Report on Patentability for International Application No. PCT/IB2015/001426, dated Nov. 19, 2015 (9 pages).
"Detection of PDGFR-alpha in Formalin-Fixed, Paraffin-Embedded Rat Tissue", National Institute of Environmental Health Sciences, Immunohistochemistry Support Group (2009) retrievied from : https://www.niehs.nih.gov/research/atniehs/labs/assets/docs/k_p/pdgfralpha_508.pdf.
Brose et al., "Rationale and design of decision: a double-blind, randomized, placebo-controlled phase III trial evaluating the efficacy and safety of sorafenib in patients with locally advanced or metastatic radioactive iodine (RAI)-refractory, differentiated thyroid cancer," BMC Cancer. 11:349 (2011) (7 pages).
Bruland et al., "Inverse correlation between PDGFC expression and lymphocyte infiltration in human papillary thyroid carcinomas," BMC Cancer. 9:425 (2009) (15 pages).
Carr et al., "Phase II study of daily sunitinib in FDG-PET-positive, iodine-refractory differentiated thyroid cancer and metastatic medullary carcinoma of the thyroid with functional imaging correlation," Clin Cancer Res. 16(21):5260-8 (2010).
Chen et al., "An aberrant autocrine activation of the platelet-derived growth factor alpha-receptor in follicular and papillary thyroid carcinoma cell lines," Cancer Lett. 231(2):192-205 (2006).
Chiu et al., "Diagnostic utility of galectin-3 in thyroid cancer," Am J Pathol. 176(5):2067-81 (2010).
Cooper et al., "Revised American Thyroid Association management guidelines for patients with thyroid nodules and differentiated thyroid cancer," Thyroid. 19(11):1167-1214 (2009) (31 pages).
Cornella et al., "Molecular pathogenesis of hepatocellular carcinoma," Alcohol Clin Exp Res. 35(5):821-5 (2011).
Crowe et al., "The impact of implementation of the Bethesda System for Reporting Thyroid Cytopathology on the quality of reporting, "risk" of malignancy, surgical rate, and rate of frozen sections requested for thyroid lesions," Cancer Cytopathol. 119(5):315-21 (2011).
Dean et al., "Epidemiology of thyroid nodules," Best Pract Res Clin Endocrinol Metab. 22(6):901-11 (2008).
DeLellis, "Pathology and genetics of thyroid carcinoma," J Surg Oncol. 94(8):662-9 (2006).
Eckert et al., "Twist1-induced invadopodia formation promotes tumor metastasis," Cancer Cell. 19(3):372-86 (2011) (23 pages).
Elaraj et al., "Changing management in patients with papillary thyroid cancer," Curr Treat Options Oncol. 8(4):305-13 (2007).
Gharib et al., "Fine-needle aspiration biopsy of the thyroid: an appraisal," Ann Intern Med. 118(4):282-9 (1993).
Gild et al., "Multikinase inhibitors: a new option for the treatment of thyroid cancer," Nat Rev Endocrinol. 7(10):617-24 (2011).
Griffith et al., "Biomarker panel diagnosis of thyroid cancer: a critical review," Expert Rev Anticancer Ther. 8(9):1399-413 (2008).
Griffith et al., "Meta-analysis and meta-review of thyroid cancer gene expression profiling studies identifies important diagnostic biomarkers," J Clin Oncol. 24(31):5043-51 (2006).
Gu et al., "Association of XIAP and P2X7 receptor expression with lymph node metastasis in papillary thyroid carcinoma," Endocrine. 38(2):276-82 (2010).

Gupta-Abramson et al., "Phase II trial of sorafenib in advanced thyroid cancer," J Clin Oncol. 26(29):4714-9 (2008).
Homsi et al., "Spectrum of activity and mechanism of action of VEGF/PDGF inhibitors," Cancer Control. 14(3):285-94 (2007).
International Report on Patentability and the Written Opinion of the International Searching Authority for International Application No. PCT/CA2013/000090, dated Aug. 5, 2014 (8 pages).
International Search Report and Written Opinion of the International Searching Authority for International Application No. PCT/CA2013/000090, dated Apr. 29, 2013 (12 pages).
Ito et al., "Lateral lymph node dissection guided by preoperative and intraoperative findings in differentiated thyroid carcinoma," World J Surg. 32(5):729-39 (2008).
Kloos et al., "Phase II trial of sorafenib in metastatic thyroid cancer," J Clin Oncol. 27(10):1675-84 (2009).
Lee et al., "Expression of cell-cycle regulators (cyclin D1, cyclin E, p27kip1, p57kip2) in papillary thyroid carcinoma," Otolaryngol Head Neck Surg. 142(3):332-7 (2010).
Lei et al., "Pathological signaling via platelet-derived growth factor receptor alpha involves chronic activation of Akt and suppression of p53," Mol Cell Biol. 31(9):1788-99 (2011).
Liang et al., "Assessment of biomarkers for clinical diagnosis of papillary thyroid carcinoma with distant metastasis," Int J Biol Markers. 25(1):38-45 (2010).
Liu et al., "PDGF-D improves drug delivery and efficacy via vascular normalization, but promotes lymphatic metastasis by activating CXCR4 in breast cancer," Clin Cancer Res. 17(11):3638-48 (2011).
Lundgren et al., "Clinically significant prognostic factors for differentiated thyroid carcinoma: a population-based, nested case-control study," Cancer. 106(3):524-31 (2006).
Machens et al., "Pattern of nodal metastasis for primary and reoperative thyroid cancer," World J Surg. 26(1):22-8 (2002).
Marchetti et al., "A morpho-molecular diagnosis of papillary thyroid carcinoma: BRAF V600E detection as an important tool in preoperative evaluation of fine-needle aspirates," Thyroid. 19(8):837-42 (2009).
Morgenthau et al., "Recent advances in sarcoidosis," Chest. 139(1):174-82 (2011).
Nikiforov et al, "Impact of mutational testing on the diagnosis and management of patients with cytologically indeterminate thyroid nodules: a prospective analysis of 1056 FNA samples," J Clin Endocrinol Metab. 96(11):3390-7 (2011).
Nikiforov, "Thyroid carcinoma: molecular pathways and therapeutic targets," Available in PMC May 1, 2009, published in final edited form as: Mod Pathol. 21(Suppl 2):S37-43 (2008).
Provencio et al., "Clinical-molecular factors predicting response and survival for tyrosine-kinase inhibitors," Clin Transl Oncol. 11(7):428-36 (2009).
Rojo et al., "Review of imaging solutions for integrated quantitative immunohistochemistry in the Pathology daily practice," Folia Histochem Cytobiol. 47(3):349-54 (2009).
Romagnoli et al., "Targeted molecular therapies in thyroid carcinoma," Arg Bras Endocrinol Metabol. 53(9):1061-73 (2009).
Rotstein, "The role of lymphadenectomy in the management of papillary carcinoma of the thyroid," J Surg Oncol. 99(4):186-8 (2009).
Russell et al., "The alpha-receptor for platelet-derived growth factor confers bone-metastatic potential to prostate cancer cells by ligand- and dimerization-independent mechanisms," Cancer Res. 70(10):4195-203 (2010) (12 pages).
Schweppe et al., "Deoxyribonucleic acid profiling analysis of 40 human thyroid cancer cell lines reveals cross-contamination resulting in cell line redundancy and misidentification," J Clin Endocrinol Metab. 93(11):4331-41 (2008).
Shaha et al., "Patterns of failure in differentiated carcinoma of the thyroid based on risk groups," Head Neck. 20(1):26-30 (1998).
Sherman, "Targeted therapies for thyroid tumors," Mod Pathol. 24 Suppl 2:S44-52 (2011).
Shibru et al., "Does the 3-gene diagnostic assay accurately distinguish benign from malignant thyroid neoplasms?" Cancer. 113(5):930-5 (2008).

(56) References Cited

OTHER PUBLICATIONS

Shibru et al., "Recent developments in the clinical application of thyroid cancer biomarkers," Curr Opin Oncol. 20(1):13-8 (2008).
Sywak et al., "Routine ipsilateral level VI lymphadenectomy reduces postoperative thyroglobulin levels in papillary thyroid cancer," Surgery. 140(6):1000-7 (2006).
Taccaliti et al., "Genetic mutations in thyroid cancer," Minerva Endocrinol. 34(1):11-28 (2009).
Tambouret et al., "The clinical application and cost analysis of fine-needle aspiration biopsy in the diagnosis of mass lesions in sarcoidosis," Chest. 117(4):1004-11 (2000).
Tee et al., "Fine-needle aspiration may miss a third of all malignancy in palpable thyroid nodules: a comprehensive literature review," Ann Surg. 246(5):714-20 (2007).
Udelsman, "Treatment of persistent or recurrent papillary carcinoma of the thyroid—the good, the bad, and the unknown," J Clin Endocrinol Metab. 95(5):2061-3 (2010).
Wang et al., "Association of the T1799A BRAF mutation with tumor extrathyroidal invasion, higher peripheral platelet counts, and over-expression of platelet-derived growth factor-B in papillary thyroid cancer," Endocr Relat Cancer. 15(1):183-90 (2008).
Wang et al., "Serine phosphorylation of NPM-ALK, which is dependent on the auto-activation of the kinase activation loop, contributes to its oncogenic potential," Carcinogenesis. 32(2):146-53 (2010).
Yano et al., "Gene expression profiling identifies platelet-derived growth factor as a diagnostic molecular marker for papillary thyroid carcinoma," Clin Cancer Res. 10(6):2035-43 (2004).
Yip et al,. "Summary statement: utility of molecular marker testing in thyroid cancer," Available in PMC Dec. 1, 2011, published in final edited form as: Surgery. 148(6):1313-5 (2010) (4 pages).
Zatelli et al., "BRAF V600E mutation analysis increases diagnostic accuracy for papillary thyroid carcinoma in fine-needle aspiration biopsies," Eur J Endocrinol. 161(3):467-73 (2009).
Zhu et al., "Diagnostic significance of CK19, RET, galectin-3 and HBME-1 expression for papillary thyroid carcinoma," J Clin Pathol. 63(9):786-9 (2010) (5 pages).

* cited by examiner

US 10,266,603 B2

TARGETED THERAPY TO RESTORE RADIOACTIVE IODINE TRANSPORT IN THYROID CANCER

RELATED APPLICATIONS

This application claims priority under 35 U.S.C. § 119(e) to U.S. Provisional Patent Application No. 61/981,358, filed Apr. 18, 2014, which application is incorporated herein by reference in its entirety.

FIELD OF THE INVENTION

The invention relates generally to methods, compositions and uses thereof for treatment of individuals that are diagnosed with papillary thyroid carcinoma.

BACKGROUND OF THE INVENTION

Papillary thyroid carcinoma (PTC) comprises 90% of all cases of thyroid cancer. Thyroid cancer is now the $4^{th}$ or $5^{th}$ most common cancer in women in Western Countries and more than 71,000 patients in North America will be treated this year. Treatment of PTC typically requires a total thyroidectomy followed by radioactive iodine treatment to remove small deposits of residual tumor. Clinicians rely on criteria such as tumor size and clinical presentation to predict the risks of metastatic disease.

However, these measures are inaccurate in over 30% of cases and patients with larger indolent tumors can be over treated while aggressive smaller tumors with a high propensity for metastases are undertreated. In addition, more than 40% of PTC patients exhibit some degree of resistance to adjuvant radioiodine therapy due to down-regulation of the sodium-iodide symporter (NIS) that is responsible for iodine uptake in thyroid cells. These patients ultimately have higher rates of recurrent disease and a poorer prognosis.

Accordingly, there is a need for a method to effectively treat PTC that restores radioiodine sensitivity to PTC cells to eliminate or greatly reduce PTC.

SUMMARY

The Applicant's have identified platelet derived growth factor receptor alpha (PDGFRA) (Zhang et al., *J. Pathology* 2012; 228:241) as a specific and novel diagnostic marker for metastatic papillary thyroid carcinoma (PTC). Large-scale patient tissue arrays as well as extensive in vitro and mouse xenograft experiments have demonstrated the essential role of PDGFRA in driving metastatic disease. The Applicants now show in vitro and in vivo data indicating that targeted therapy disrupting PDGFRA signaling may be a potent tool to restore radioactive iodine sensitivity in thyroid cancer patients as well as directly decreasing tumor burden in patients with aggressive PTC variants. This novel marker can be the backbone of a new paradigm for combining radioactive iodine treatments with targeted small molecule and antibody therapy for papillary thyroid cancer.

Accordingly, the disclosure provides for a method and use for treating a patient with papillary thyroid carcinoma comprising administering a therapeutically effective amount of at least one PDGFRA inhibitor, or a pharmaceutically acceptable salt thereof, to a patient with papillary thyroid cancer, wherein the administering of the PDGFRA inhibitor treats or reduces the severity of papillary thyroid carcinoma symptoms.

In another embodiment, the PDGFRA inhibitor causes a decrease in PDGFRA expression and/or inactivates or reduces the activity of PDGFRA.

In another embodiment, the PDGFRA inhibitor increases a PTC cell's sensitivity to radioiodine treatment.

In another embodiment, the PDGFRA inhibitor is an antibody or fragment thereof. The antibody can be used in conjunction with another PDGFRA inhibitor or a chemotherapeutic agent.

In some embodiments, the other PDGFRA inhibitor is a tyrosine kinase inhibitor or an RNA interference molecule.

In another embodiment, the antibody or fragment thereof is specific for PDGFRA. The antibody or fragment thereof may be a monoclonal or polyclonal antibody.

In another embodiment, a method and use for treating a patient with papillary thyroid carcinoma is provided for, the method or use comprising administering a therapeutically effective amount of at least one PDGFRA inhibitor, or a pharmaceutically acceptable salt thereof, to a patient with papillary thyroid cancer, the PDGFRA inhibitor being an antibody, or a fragment thereof, that is specific to PDGFRA, wherein the administering of the PDGFRA inhibitor treats or reduces the severity of papillary thyroid carcinoma symptoms. The method or use can have an antibody or fragment thereof that is specific for PDGFRA.

In some embodiments, the antibody or fragment thereof can increase the sensitivity of a papillary thyroid carcinoma cell to radioiodine treatment. The antibody can be used with another tyrosine kinase inhibitor or a chemotherapeutic agent.

In still a further embodiment, a pharmaceutical composition for the treatment of papillary thyroid carcinoma comprising a PDGFRA inhibitor, or a pharmaceutically acceptable salt or solvate thereof, and a pharmaceutically acceptable carrier or excipient is provided.

In some embodiments, the inhibitor is an antibody or fragment thereof that is specific for PDGFRA. The antibody can be used in conjunction with a tyrosine kinase inhibitor, an RNA interference molecule or another chemotherapeutic agent.

Another embodiment provides for an isolated PDGRA inhibitor, or a pharmaceutically acceptable salt or solvate thereof.

Further embodiments provide for the use of a PDGFRA inhibitor, or a pharmaceutically acceptable salt thereof to treat a patient having papillary thyroid carcinoma.

In other embodiments, the use of a PDFGRA inhibitor is an antibody or fragments thereof, a tyrosine kinase inhibitor, an RNA interference molecule or a combination thereof that increases the iodine sensitivity in the patient.

In still further embodiments, there is provided herein a method and use for treating a patient with papillary thyroid carcinoma comprising obtaining a first biological sample from a patient having or is suspected of having papillary thyroid carcinoma, determining the level of at least one biomarker in the sample obtained from the patient, administering a first treatment to the patient, making a second measurement of the biomarker from a second sample obtained from the patient and comparing the levels of the biomarker after the first treatment to the levels of the same biomarker before the first treatment, determining that the patient has a change in the level of the biomarker and administering a second treatment to the patient wherein the second treatment treats or reduces the severity of the PTC symptoms.

In other embodiments, the biomarker is PDFGRA, TTF-1, NIS or a combination of thereof.

In other embodiments, the change in the level of biomarker can be a decrease in PDGFRA, an increase in TTF-1 or an increase in NIS. The increase or decrease can be in the protein level, protein activity, mRNA transcripts or a combination thereof.

In other embodiments, the level of the at least one biomarker is compared to the levels of the at least one biomarker in a sample known to have PTC.

In other embodiments, the first treatment comprises a PDFGRA inhibitor.

In other embodiments, the PDGFRA inhibitor is an antibody, tyrosine kinase inhibitor, an RNA interference molecule or a combination thereof.

In some embodiments, the first treatment increases the iodine sensitivity of the patient. The first treatment may also treat or reduce the severity of PTC symptoms.

In further embodiments, the second treatment is radioiodine ablation therapy. The second treatment may also further comprise a PDGFRA inhibitor.

In other embodiments, there is provided herein a method and use for treating a person having papillary thyroid carcinoma comprising obtaining a biological sample from a patient, determining the levels of at least one of PDGFRA, NIS, or TTF-1 protein levels, mRNA or protein activity in the sample obtained from the patient, administering a first treatment to the patient, making a second measurement of the at least one levels of PDGFRA, NIS, or TTF-1 protein levels, mRNA levels or protein activity from a second sample obtained from the patient after the first treatment and comparing these levels of PDGFRA, NIS, or TTF-1 protein levels, mRNA levels or protein activity to the first sample before the first treatment, determining that the patient has a change in the levels of PDGFRA, NIS, or TTF-1 protein levels, mRNA levels or protein activity and administering a second treatment to the subject wherein the second treatment is radioiodine ablation therapy.

In other embodiments, the papillary thyroid carcinoma is metastatic or recurrent papillary thyroid carcinoma.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1A:
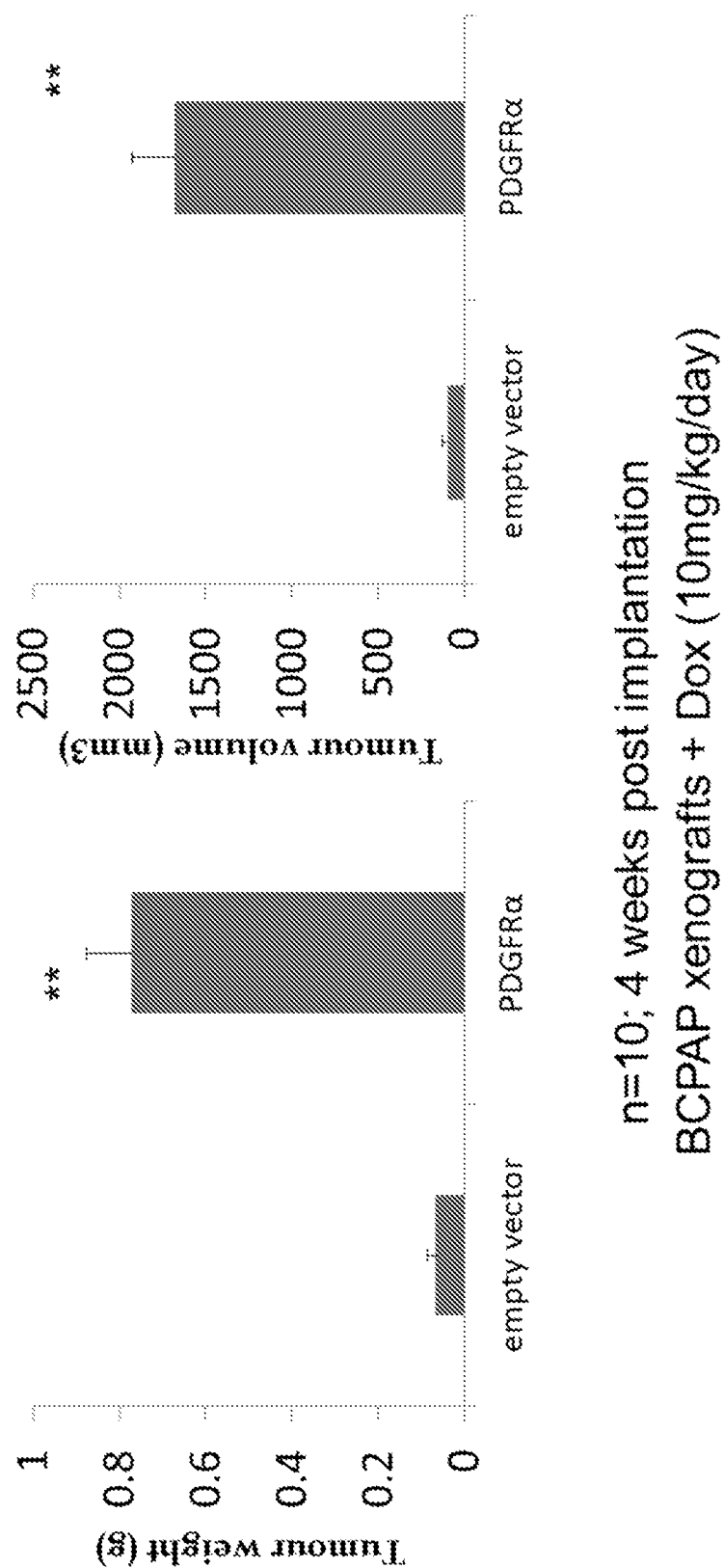
FIG. 1. (A) Human papillary thyroid cancer cell line BCPAP xenograft tumor growth with and without expression of the PDGFRA subunit. The empty vector represents the native cell line with an empty vector inserted into genome as a control with the other cell line expressing PDGFRA. It is clear by both weight and volume that the expression of PDGFRA in BCPAP xenograft cells leads to a significant increase in tumor weight and volume. At all time points during the experiment the rate of growth of the PDGFRA xenograft was much faster than the empty vector. (B) Representative photograph taken at time of sacrifice for SCID mouse BCPAP xenograft model. (C) The transfected alpha subunit of PDGFR is shown on the left of the figure with the much smaller native tumor shown on the right side. This representative photograph was replicated in every single SCID xenograft experiment where BCPAP papillary thyroid carcinoma tumors were between 5 to 10 times larger than the native tumors (n=8).

Recent studies involving large patient series indicate that platelet derived growth factor receptor alpha (PDGFRA) drives nodal metastases in PTC and promotes radioactive iodine resistance. We found that more than 90% of all metastatic PTC specimens tested to date exhibit PDGFRA, but benign or local tumors rarely express this protein (<10%). In cell culture we have shown that PDGFRA drives aggressive disease by inducing cell dedifferentiation and disrupted function of the sodium iodide symporter. In vivo, the Applicants see a decreased ability of cells to concentrate therapeutic levels of radioactive iodine and we demonstrate in human PTC specimens that PDGFRA drives metastases through activation of the mitogen activated protein kinase and phosphatidyinositol-3-kinase pathways. Our SCID mice xenograft tests in multiple cell lines reveal that tumors expressing PDGFRA are at least 5× greater by size, and more invasive, than tumors lacking PDGFRA.

Therefore, PDGFRA represents a novel and specific target for metastatic PTC. Novel tyrosine kinase inhibitor (TKI) or antibody treatments to disrupt the function of this tyrosine kinase receptor will provide a "1-2 punch" to treat thyroid cancer. Firstly, down regulation of, or inactivation of, PDGFRA may restore radioiodine sensitivity in patients with PTC. Secondly, a PDGFRA blockade may directly disrupt tumor growth and the formation of metastases. All previous attempts to use adjuvant drug therapy to treat metastatic PTC failed for 75% or more of patients (or were intolerable), due to the fact these drugs incompletely block PDGFRA signaling. Patients with thyroid cancer, of which 50% or more are at risk of metastases, can benefit from use of a TKI or a PDGFRA antibody as an adjuvant therapy to decrease tumor burden and also as pre-treatment for radioactive iodine ablation to boost uptake.

These findings can readily be translated into a viable therapy by testing small molecule and antibody blockade of PDGFRA in mouse xenografts to evaluation and use in patients with advanced thyroid cancer. This work represents a significant advance to personalized, targeted therapy for thyroid cancer and has an extensive foundation of clinical and in vivo data.

Methods of Treatment

In North America alone, nearly 71,000 patients are diagnosed yearly with papillary thyroid carcinoma (PTC) and ⅔ of these patients will be assessed and treated for metastatic disease. For the first time, targeted therapy for these patients is available now that there is a clear link between metastatic disease and PDGFRA expression. Resistance to radioactive iodine and lymphatic metastases are common problems in PTC and there are no current clinically accepted therapies to address this disease beyond aggressive, repeated surgery. Based on accepted guidelines, approximately 40,000 patients in North America will receive radioactive iodine to treat metastatic disease and all of these patients are candidates for the use of targeting PDGFRA to enhance radioactive iodine uptake. Accordingly, a PDGFRA antibody or other inhibitor can be used as a treatment over a time period, such as one to two months, prior to and during the initial phases of the radioiodine therapy to increase radioiodine uptake.

The methods described herein can also be used for patients with advanced metastatic disease as a maintenance therapy to control disease severity. Over 150,000 patients in North America may be suitable for treatment given a 5-10% prevalence of aggressive disease and the typical survival time of 5-10 years (that may be extended with treatment). This could drastically decrease the number of patients requiring repeat surgery for PTC metastases. This targeted treatment approach for metastatic thyroid cancer is novel and represents a significant advancement in care. This disclosure reports the first antibody treatment to restore radioactive iodine sensitivity, and the first use of PDGFRA to treat thyroid tumor lymphatic metastases.

As described herein, the Applicant's outline the therapeutic use of PDGFRA antibodies or other inhibitors in treating radioactive iodine resistance as well as slowing tumor growth. The Applicants have refined the use of PDGFRA blockade for restoring radio-iodide transport in PTC. PDGFRA blockade can also be used as a means to slow metastatic tumor growth in PTC. Novel antibodies or inhibitors and sequences for PDGFRA blockade can be used to optimize treatment effects for inhibiting or slowing tumor growth as well as restoring iodide transport.

In some embodiments, a method for the treatment of a patient with a likelihood of developing or having metastatic PTC comprises administering to the patient an inhibitor of PDGFRA. Inhibitors of PDGFRA include RNA interference molecule, a small molecule, nucleic acid, an antibody, a peptide, an aptamers, or combinations thereof. Preferably, the inhibitor increases radioiodine sensitivity in cancerous cells. Preferably, the PDGFRA inhibitor also causes a decrease in the level of PDGFRA protein, protein activity, mRNA transcripts or combination thereof. In other embodiments, the PDGFRA inhibitor causes a decrease in the expression level of PDGFRA.

In other embodiments, the patient is also administered a therapeutically effective amount of radioiodine in addition to the PDGFRA inhibitor.

Antibodies have the ability to slow tumor growth and/or restore radioactive iodine sensitivity in PTC. There are multiple uses of PDGFRA antibody, including a diagnostic role for this antibody as well as a therapeutic role (i.e., radioactive iodine treatments or treatment to slow tumor growth). PDGFRA therapeutic antibodies also have the potential to expand into other large metastatic cancer markets such as breast, hepatocellular, and neuroendocrine cancers.

The term "antibody" as used herein, collectively means proteins, whether natural or wholly or partially synthetically produced, that participate in the body's protective immunity by selectively acting against antigens. Antibodies are composed of two identical light chains and two identical heavy chains. The light and heavy chains comprise variable and constant regions. There are five distinct types of heavy chains based on differences in the amino acid sequences of their constant regions: gamma (γ), mu (μ), alpha (a), delta (δ) and epsilon (ε) types, and the heavy chains include the following subclasses: gamma 1 (γ1), gamma 2 (γ2), gamma 3 (γ3), gamma 4 (γ4), alpha 1 (α1) and alpha 2 (α2). Also, there are two types of light chains based on differences in the amino acid sequences of their constant regions: kappa (κ) and lambda (λ) types (Coleman et al., *Fundamental Immunology*, 2nd Ed., 1989, 55-73). According to the features of the constant regions of the heavy chains, antibodies are classified into five isotypes: IgG, IgA, IgD, IgE and IgM.

Antibodies are known to generate several structurally different fragments, which include Fab, F(ab'), F(ab')2, Fv, scFv, Fd and Fc. Among the antibody fragments, Fab contains the variable regions of the light chain and the heavy chain, the constant region of the light chain and the first constant region ($C_H1$) of the heavy chain, and has a single antigen-binding site. The Fab' fragments differ from the Fab fragments in terms of having the hinge region containing one or more cysteine residues at the C-terminus (carboxyl terminus) of the heavy chain $C_H1$ domain. The F(ab')2 fragments are produced as a pair of the Fab' fragments by disulfide bonding formed between cysteine residues of the hinge regions of the Fab' fragments. Fv is the minimum antibody fragment that contains only the heavy-chain variable region and the light-chain variable region. The scFv (single-chain Fv) fragments comprise the heavy-chain variable region and the light-chain variable region that are linked to each other by a peptide linker and thus are present in a single polypeptide chain. Also, the Fd fragments comprise only the variable region and $C_H1$ domain of the heavy chain.

The term "Fc fragment", as used herein, is produced when an antibody molecule is digested with papain, and is a region of an antibody molecule except for the variable region ($V_L$) and the constant regions ($C_L$) of the light chain and the variable region ($V_H$) and the constant region 1 ($C_H1$) of the heavy chain. An Fc fragment is suitable for use as a drug carrier because it is biodegraded in vivo. Also, an Fc fragment is beneficial in terms of preparation, purification and yield of a complex with the Fc fragment because it has a small molecular weight relative to whole antibody molecules. Further, since the Fab region, which displays high non-homogeneity due to the difference in amino acid sequence between antibodies, is removed, the Fc fragment has greatly increased substance homogeneity and a low potential to induce serum antigenicity. The Fc fragment may further include the hinge region at the heavy-chain constant region. Also, the Fc fragment may be substantially identical to a native form, or may be an extended Fc fragment that contains a portion of the whole of the heavy-chain constant region 1 ($C_H1$) and/or the light-chain constant region 1 ($C_L1$) as long as it has an improved effect. Also, the Fc fragment may be a fragment having a deletion in a relatively long portion of the amino acid sequence of $C_H2$ and/or $C_H3$. A preferred Fc fragment is an IgG or IgM-derived Fc fragment.

The Fc fragment according to the present invention may be a combination or hybrid, in detail, a combination or hybrid of Fc fragments derived from IgG, IgA, IgD, IgE and IgM. The term "combination" means a dimeric or multimeric polypeptide in which single-chain Fc fragments of the same origin are linked to a single-chain Fc fragment of a different origin to form a dimer or multimer. The term "hybrid" means a polypeptide in which two or more domains of different origin is present in a single-chain Fc fragment. For example, a hybrid may be composed of one to four domains selected from among $C_H1$, $C_H2$, $C_H3$ and $C_H4$ domains contained in IgG1 Fc, IgG2 Fc, IgG3 Fc and IgG4 Fc.

The Fc fragment may be derived from humans or other animals including cows, goats, swine, mice, rabbits, hamsters, rats and guinea pigs, and preferably humans. The human-derived Fc fragment is sometimes preferable to a non-human derived Fc fragment, which may act as an antigen in the human body and cause undesirable immune responses such as the production of a new antibody against the antigen.

The antibodies used in the current invention are either polyclonal or monoclonal antibodies. In a preferred embodiment, monoclonal antibodies against PDGFRA are used. In a further preferred embodiment, the antibody to PDGFRA increases radioiodine sensitivity of a PTC cell. Monoclonal antibodies are produced, for example, by injecting a mouse, or other suitable animal, with an immunogen. The mouse is subsequently sacrificed and cells taken from its spleen are fused with myeloma cells. The result is a hybrid cell, referred to as a "hybridoma" that reproduces in vitro. The population of hybridomas is screened to isolate individual clones each of which secrete a single antibody species to the antigen. The individual antibody species obtained in this way are each the product of a single B cell from the immune animal generated in response to a specific antigenic site recognized on the immunogenic substance.

Furthermore, an antibody or antigen-binding portion thereof may be part of a larger antibody-conjugate molecule, formed by covalent or noncovalent association of the antibody or antibody portion with one or more other protein, peptides or other molecules. In some embodiments, conjugate can be formed, for example, using a peptide or nonpeptide coupling agent. In some embodiments, the effector molecule can be directly conjugated to the antibody with a linker, or without a linker.

In some embodiments, an antibody-conjugate molecule comprises a cytotoxic agent. Cytotoxic agents including any agent that is detrimental to (e g kills or inhibits the growth or dvision of) cells. Examples include combrestatins, dolastatins, epothilones, staurosporin, maytansinoids, spongistatins, rhizoxin, halichondrins, roridins, hemiasterlins, paclitaxel, cytochalasin B, gramicidin D, ethidium bromide, emetine, mitomycin, etoposide, teniposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Moreover, in some embodiments, an antibody-conjugate molecule can deliver radioiodine (e.g. $^{121}$I, $^{131}$I) directly to the cell by binding to PDGFRA.

In still further embodiments, the antibody-conjugate may also include physiologically active peptides. Such physiologically active polypeptides include various physiologically active peptides used for treating or preventing human diseases, which are exemplified by hormones, cytokines, enzymes, growth factors, transcription regulatory factors, coagulation factors, vaccines, structural proteins, ligand proteins or receptors, cell surface antigens and receptor antagonists, and derivatives and analogues thereof. Other peptides include cell internalization sequences, receptor targeting sequences and mimitopes.

Moreover, the PDGFRA antibody can be used alone or in conjunction with at least one other chemotherapeutic compound to treat metastatic cancers such as PTC. A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), leflunomide (Arava®, Sanofi Aventis, CAS No 75706-12-6) trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), and doxorubicin (ADRIAMYCIN®), Akti-½, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU1 1248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOS AR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIIVIA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammall, calicheamicin omegall (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin;

phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside (Ara-C); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-I1; topoisomerase inhibitor RFS 2000; difluoromethylornithine (DFMO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (NOLVADEX®; tamoxifen citrate), raloxifene, droloxifene, 4-hydroxytamoxifen, trioxifene, keoxifene, LY1 17018, onapristone, and FARESTON® (toremifme citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies including PDGFRA specific monoclonal antibodies such as Olaratumab (IMC-3G3, Eli-Lilly), MEDI-575 (MedImmune LLC) and other specific agents such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idee), pertuzumab (OMNITARG™, 2C4, Genentech), trastuzumab (HERCEPTIN®, Genentech), tositumomab (Bexxar, Corixia), and gemtuzumab ozogamicin (MYLOTARG®, Wyeth). Chemotherapeutic agents can also be conjugated to antibody to form an antibody-conjugate molecule as described above.

In some embodiments, an antibody to PDGFRA is used in conjunction with another PDGFRA inhibitor. In some embodiments, the PDGFRA inhibitor is a tyrosine kinase inhibitor. A tyrosine kinase inhibitor may also be angiokinase inhibitors, Apatinib, Axitinib, (Inlyta®) Bosutinib (Bosulif®), Cabozantinib, Canertinib, Cediranib (Recentini®) Crenolanib, Crizotinib (Xalkori®), Damnacanthal, Dasatinib (Sprycel®), Erlotinib (Tarceva®), Foretinib, Fostamatinib, Gefitinib (Iressa®), Ibrutinib, Imatinib mesylate (Gleevec®), Lapatinib (Tykerb®), Linifanib, Motesanib, Mubritinib, Nilotinib (Tasigna®), Nintedanib, Pertuzumab (Perjeta™), Pazopanib (Votrient®), Radotinib, Regorafenib (Stivarga®), Sorafenib (Nexavar®), Sunitinib (Sutent®), Vatalanib, Vandetanib (Caprelsa®) and Vemurafenib. In preferred embodiments, the tyrosine kinase inhibitors specifically inhibit PDGFRA to restore iodine sensitivity to PTC cells. In other embodiments, the tyrosine kinase inhibitors act upon downstream signaling proteins such as, for example, members of the Phosphoinositide-3-kinase/Akt pathway to inhibit PTC.

In some embodiments, the PDGFRA inhibitor is an RNA interference molecule. RNA interference molecules comprise, for example, an RNAi molecule, a siRNA molecule, or an shRNA molecule. The term siRNA (short interfering RNA) or siRNA duplexes, as used herein has the same meaning as typically in the art. i.e. the term siRNA refers to double stranded RNA complex. Often, the complex has 3'-overhangs. SiRNA can be made using techniques known to one skilled in the art. Other siRNA's are commercially available.

These molecules can be delivered to the patient using techniques that are well known to those skilled in the art. RNA interference molecules and other compounds can be used to decrease the expression (for example, at the transcriptional, translational or post-translational level) of PDGFRA in the cell and/or by inhibiting PDGFRA activity. In some embodiments, more than one PDGFRA inhibitor can be used to treat PTC. For example, an antibody or fragment thereof specific for PDGFRA can be used in conjunction with an RNA interference molecule or a tyrosine kinase inhibitor or a combination thereof.

In some embodiments, aptamers can be used to target and inhibit PDGFRA. Aptamers are single stranded DNA or RNA molecules that can bind to pre-selected targets such as proteins or peptides with high affinity. These molecules can be engineered to bind to a specific target through selective binding in vitro. Thus, an aptamer can be designed for virtually any desired target. Therefore, an aptamer or a plurality thereof can be used to specifically bind to PDGFRA on the cell surface, thereby disrupting PDGFRA activity and restoring radioiodine sensitivity. Aptamers can be used in conjunction with other PDGFRA inhibitors to treat PTC.

In addition to treating PTC, PDGFRA can be used as a diagnostic biomarker for PTC. The term "biomarker" as used herein refers to a marker that informs about the outcome of a patient in the absence of systemic therapy or portends an outcome different from that of the patients without the marker, despite empiric (not targeted to the marker) systemic therapy.

PDGFRA can be measured/detected by a variety of techniques known to the skilled worker, including, but not limited to, immunoprecipitation, immunoblotting, mass spectrometry, quantitative fluorescence activated cell sorting, enzyme linked immunosorbent assay, immunofluorescence, radio-labeling, immunohistochemistry, quantitative immunohistochemistry, fluorescence resonance energy transfer, Forster resonance energy transfer, and biomolecular fluorescence complementation.

In other examples, PDGFRA is detected using a binding agent including, but not limited to, a lectin, nucleic acid (e.g.

DNA, RNA), monoclonal antibody, polyclonal antibody, Fab, Fab', single chain antibody, synthetic antibody, aptamer (DNA/RNA), peptoid, zDNA, peptide nucleic acid (PNA), locked nucleic acid (LNA), synthetic or naturally occurring chemical compound (including but not limited to a drug or labeling reagent), dendrimer, or any combination thereof. In some instances, a single agent is used to detect a biomarker. In other instances, a combination of different agents is used to detect a biomarker The term "label" as used herein is an identifiable substance that is detectable in an assay and that can be attached to a molecule creating a labeled molecule. The behavior of the labeled molecule can then be monitored and/or studied and/or detected.

Examples of labels include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate. The particular label used will depend upon the type of immunoassay. Antibodies can be tagged with such labels by known methods.

In some embodiments, the methods or use presented herein for treatment of a person having or suspected of having PTC comprises 1) obtaining a biological sample from a patient 2) determining the level of the biomarker in the sample obtained from the patient 3) administering a first treatment to the patient 4) making a second measurement of the biomarker from a second sample obtained from the patient after the first treatment and comparing the levels of the biomarker to the same biomarker before the first treatment 5) determining that the patient has a change in the level of biomarker and 6) administering a second treatment to the subject wherein the second treatment treats or reduces the severity of the PTC symptoms. In other embodiments, the first treatment also treats or reduces the severity of the PTC symptoms.

As used herein, "obtaining a sample" or "obtaining a biological sample" refers to such methods as will be well known to the skilled worker. A biological sample may be obtained directly or indirectly from the subject. The term "obtaining" a biological sample may comprise receiving a biological sample from an agent acting on behalf of the subject. For example, receiving a biological sample from a doctor, nurse, hospital, medical center, etc., either directly or indirectly, e.g. via a courier or postal service. In some cases the biological sample is obtained from archival repositories. In one example, the methods of the invention are carried out in vitro or ex vivo.

In other examples, a sample containing cancerous cells or suspected as containing cancerous cells is obtained from the subject which is at risk for PTC, is suspected of having PTC, and/or has been diagnosed with PTC can be collected using a fine needle aspirate (FNA) sample. Methods of obtaining a FNA sample, processing and/or storage of such a sample are also well known to the skilled worker. In other examples, a sample is obtained from surgical dissection. In other embodiments, a physician prepares the samples or other qualified individual and provided for examination.

The term "sample" as used herein, encompasses a variety of cells, cell-containing bodily fluids and/or secretions as well as tissues including, but not limited to a cell(s), tissue, whole blood, blood-derived cells, plasma, serum, sputum, mucous, bodily discharge, and combinations thereof, and the like.

In one embodiment, a method as described herein comprises qualitatively or quantitatively determining, analyzing or measuring a biological sample from a subject for the presence or absence, or amount or concentration, of one or more prognostic marker (or biomarker) associated with the diagnosis and/or prognosis and/or therapeutic monitoring of metastatic cancer or recurrent cancer. In other embodiments, the cancer is metastatic PTC or recurrent PTC.

In one example, in determining whether there is an increase, decrease or no change in amount of the biomarker, the patient sample may be compared to one or more control samples. In one example, a control sample has had known and/or established level of the biomarker. In one example, a control sample is a patient sample that has known and/or established levels of biomarker expression and/or known clinical outcome (e.g. PTC). In one example, a control is a cell line that has a known amount of biomarker expression. In another example, the control sample is taken from the subject prior to treatment or a treatment step. In some examples, a control is not used and qualitative or quantitative methods are used to determine the presence or absence, or amount or concentration of the protein of interest.

In some embodiments, the biomarker is a protein, enzymatic activity or an mRNA transcript or a combination thereof.

Biomarker protein can be measured or detected by a variety of techniques known to the skilled worker, including, but not limited to, immunoassays using a biomarker specific antibody. Protein levels can also be determined using a specific antibody or mass spectroscopy in conjunction with 2 dimensional gel electrophoresis (separation of proteins by their isoelectric point (IEF) in the first dimension followed by molecular weight determination using sodium dodecyl sulphate polyacrylamide gel electrophoresis (SDS-PAGE)).

Biomarker transcripts or mRNA can be measured using any of many techniques known to those of skill in the art, including, but not limited to, northern hybridization, PCR, reverse transcription followed by PCR, quantitative real-time PCR, nuclease protection assay, and in situ hybridization.

Biomarker activity can be measured by a variety of assays known to those of skill in the art. A suitable method can be selected to determine the activity of proteins encoded by the biomarker genes according to the activity of each protein analyzed. For biomarker proteins, polypeptides, isoforms, mutations, and variants thereof known to have enzymatic activity, the activities can be determined in vitro using enzyme assays known in the art. Such assays include, without limitation, protease assays, kinase assays, phosphatase assays, reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

In some embodiments, the biomarker is PDGFRA. Generally, in subjects with PTC, the presence of PDGFRA is higher when compared to control sample.

Figure 6:
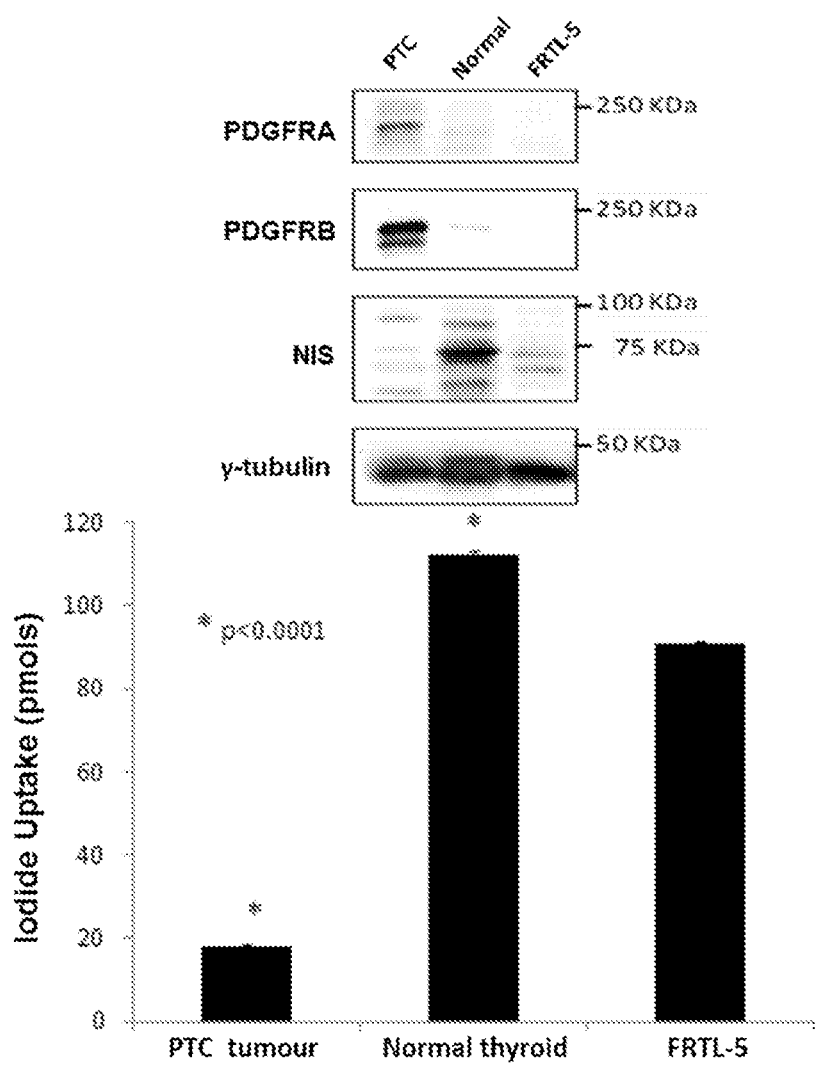
FIG. 6. In primary cultures of human papillary thyroid carcinomas, we find that expression of PDGFRA as shown by the western blot panel is associated with a decreased expression of the sodium iodide symporter and as a result these tumor cells are not capable of transporting iodide into the cell (bottom panel) which effectively renders them resistant to radioactive iodine therapy which is standard for patients with papillary thyroid carcinoma.

In other embodiments, it may be useful to monitor other biomarkers either separately, or in conjunction with PDGFRA. For example, biomarkers can be the sodium iodide symporter (NIS) that is essential for concentrating radioactive iodine. In the presence of increased PDGFRA, (such as in PTC) the level of NIS protein is drastically reduced (see FIG. 6).

In other embodiments, the biomarker can be thyroid transcription factor-1. Thyroid transcription factor-1 (TTF- 1) is a nuclear homeo-domain transcription factor that is expressed in the developing thyroid, respiratory epithelium, and diencephalon. The Applicants have shown that in the presence of increased levels of PDGFRA, the levels of TTF-1 are also dramatically reduced (see FIGS. 2 and 3). TTF-1, along with another transcription factor, Pax-8, are needed for expression of NIS. A reduction of TTF-1 results in a concomitant reduction in NIS, thereby reducing the iodine sensitivity of the patient (see FIG. 7).

Based upon the finding of the presence, absence or changes in levels of biomarker(s), a first treatment can be administered to the subject. The treatment, as discussed previously can be inhibitors of PDGFRA that include RNA interference molecule, a small molecule (e.g. tyrosine kinase inhibitors or other known small molecule PDGFRA inhibitors like sorafenib, sunitinib, axitinib, crenolanib or motisanib), nucleic acid, an antibody or fragment thereof, a peptide, aptamers, or pharmaceutically acceptable salt thereof or combinations thereof. The first treatment can administered over a variety of different time periods that can be from 1-2 weeks, 1-3 weeks, 1-4 weeks, 1-5 weeks, 1-6 weeks or until the measured biomarker shows a response to the treatment. In other embodiments, the first treatment is a pre-treatment of 4-6 weeks prior to administering the second treatment.

In some embodiments, as an example, it is expected that in a response to the first treatment, the levels of PDGFRA mRNA levels, protein, or the activity thereof would decrease in the presence of a PDGFRA inhibitor. In other examples, it would be expected that the levels of NIS protein would increase, as would the level of TTF-1 protein in samples that are positively responding to the first treatment when compared to an appropriate control sample, such as a sample known to be positive for PTC, or more preferably, a sample from the subject prior to treatment.

In samples that are positive controls for PTC, it would be expected that the levels of PDGFRA would be higher, and the levels of TTF-1 and NIS would be low or absent when compared to normal samples.

In some embodiments, the treatment of the patient results in an increase in iodine uptake.

After a finding of a response to the first treatment, a second treatment can then be administered to the patient. Preferably, since the first treatment would increase the patient's sensitivity to iodine uptake (due to the decrease in PDGFRA expression or activity and the resulting increase in TTF-1 and NIS), the second treatment is preferable a radioactive iodine ablation therapy. In some embodiments, the second treatment can also include other PDGFRA inhibitors, such as those that were used in the first treatment. The second treatment may also include various forms of chemotherapy.

In further embodiments, the method and uses presented herein for treatment of a person having or suspected of having PTC comprises 1) obtaining a biological sample from a patient 2) determining the level of the levels of at least one of PDGFRA, NIS, or TTF-1 protein levels, mRNA or protein activity in the sample obtained from the patient 3) administering a first treatment to the patient 4) making a second measurement of the at least one levels of PDGFRA, NIS, or TTF-1 protein levels, mRNA levels or protein activity from a second sample obtained from the patient after the first treatment and comparing these levels of PDGFRA, NIS, or TTF-1 protein levels, mRNA levels or protein activity to first sample before the first treatment 5) determining that the patient has a change in the levels of PDGFRA, NIS, or TTF-1 protein levels, mRNA levels or protein activity and 6) administering a second treatment to the subject wherein the second treatment is radioiodine ablation therapy.

In some embodiments, the treatment of a subject with a PDGFRA inhibitor such as an antibody or fragment thereof causes an increase of at least 20%, at least 30%, at least 40%, at least 50%, at least 60%, at least 70%, at least 80%, at least 90% at least 100%, at least 150%, at least 200%, at least 250%, at least 300%, at least 350%, at least 400% or at least 450% increase of iodine uptake as compared to iodine uptake in PTC cells.

Pharmaceutical Formulations

In addition to the methods described herein, the present disclosure also provides for a pharmaceutical composition comprising at least a PDGFRA inhibitor. The present disclosure also provides for an isolated PDGFRA inhibitor.

In an embodiment, a pharmaceutical composition for the treatment of papillary thyroid cancer is provided comprising a PDGFRA inhibitor, or a pharmaceutically acceptable salt or solvate thereof, and a pharmaceutically acceptable carrier or excipient. The pharmaceutical composition may also include a chemotherapeutic agent, a PDGFRA inhibitor, a tyrosine kinase inhibitor, an antibody to PDGFRA, an RNA interference molecule or a combination thereof. Moreover, the pharmaceutical composition may be configured to increase the sensitivity of a papillary thyroid carcinoma cell to radioiodine treatment. In another embodiment, the pharmaceutical composition reduces the expression of PDGFRA in a cancer cell. In yet another embodiment, the pharmaceutically composition is configured to reduce PDGFRA expression (via a reduction of PDGFRA mRNA or protein levels) in a cell and/or inhibit PDGFRA activity of the cancer cell.

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intra-peritoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Agents delaying absorption, for example, aluminum monostearate and/or gelatin can bring about prolonged absorption of the injectable compositions.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. Nos. 4,992,478 (Geria), 4,820,508 (Wortzman), 4,608,392 (Jacquet et al.), and 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivaative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The disclosure provides therapeutic methods of treating cancer, particularly metastatic PTC, in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known.

In another embodiment, an isolated PDGRA inhibitor, or a pharmaceutically acceptable salt or solvate thereof is provided. In some embodiments, the isolated PDGFRA is an antibody or a fragment there of that specifically binds to PDGFRA. In some embodiments, the antibody or fragment thereof that binds to PDGFRA increases the sensitivity of a papillary thyroid carcinoma cell to radioiodine therapy. In other embodiments, the isolated PDGFRA inhibitor is an antibody that binds to PDGFRA and inhibits PDGFRA activity.

Definitions

The following definitions are included to provide a clear and consistent understanding of the specification and claims. As used herein, the recited terms have the following meanings. All other terms and phrases used in this specification have their ordinary meanings, as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "subject" or "patient" as used herein, refers to any mammal or non-mammal that would benefit from determining the benefit from treatment, treatment, diagnosis, therapeutic monitoring, and/or prognosis. In certain examples a subject or patient includes, but is not limited to, humans, farm animals (cows, sheep, pigs, and the like), companion animals (such as cats, dogs and horses, and the like), non-human primates and rodent (such as mice and rats). In a specific embodiment, the subject is a human.

The term "expression", as used herein, and for example in reference PDGFRA, refers to all indicators of transcriptional expression of the PDGFRA encoding gene. Such indicators include PDGFRA transcript products, generated as a result of transcription of the PDGFRA gene; translation products, including all forms of the PDGFRA protein, generated as a result of translation of the PDGFRA transcripts; and demonstrable or otherwise measurable PDGFRA activity.

As used herein, the term "fragment" refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a primary or secondary effector molecule.

As used herein, the term "isolated" in the context of a peptide, polypeptide, fusion protein, antibody or antigen-binding antibody fragment refers to a peptide, polypeptide, fusion protein, antibody or antigen-binding antibody fragment which is substantially free of cellular material or contaminating proteins from the cell or tissue source from which it is derived or obtained, or substantially free of chemical precursors or other chemicals when chemically synthesized. The language "substantially free of cellular material or contaminating protein" includes preparations of a peptide, polypeptide, fusion protein, antibody or antigen-binding antibody fragment in which the peptide, polypeptide, fusion protein, antibody or antigen-binding antibody fragment is separated from cellular components of the cells from which it is isolated or recombinantly produced. Thus, a peptide, polypeptide, fusion protein, antibody or antigen-binding antibody fragment that is substantially free of cellular material or contaminating protein includes preparations of a peptide, polypeptide, fusion protein, antibody or antigen-binding antibody fragment having less than about 30%, about 20%, about 10%, or about 5% (by dry weight) of other protein. When the peptide, polypeptide, fusion protein, antibody or antigen-binding antibody fragment is recombinantly produced, it is also preferably substantially free of culture medium, i.e., culture medium represents less than about 20%, about 10%, or about 5% of the volume of the protein preparation. When the peptide, polypeptide, fusion protein, antibody or antigen-binding antibody fragment is produced by chemical synthesis, it is preferably substantially free of chemical precursors or other chemicals, i.e., it is separated from chemical precursors or other chemicals which are involved in the synthesis of the peptide, polypeptide, fusion protein, antibody or antigen-binding antibody fragment. Accordingly, such preparations of a peptide, polypeptide, fusion protein, antibody or antigen-binding antibody fragment have less than about 30%, about 20%, about 10%, about 5% (by dry weight) of chemical precursors or compounds other than the peptide, polypeptide, fusion protein, antibody The following Examples are intended to illustrate the above invention and should not be construed as to narrow its scope. One skilled in the art will readily recognize that the Examples suggest many other ways in which the invention could be practiced. It should be understood that numerous variations and modifications might be made while remaining within the scope of the invention.

EXAMPLES

Example 1. Restoring Radioactive Iodine Sensitivity in Papillary and Follicular Thyroid Cancer Current State of Radioactive Iodine Ablation for Papillary and Follicular Thyroid Carcinoma.

Papillary thyroid cancer (PTC) is an increasingly common disease.[1,2] Age-adjusted rates for thyroid cancer in North America are nearly three times higher than in 1990 and this disease is now the $4^{th}$ most common malignant disease in women. In North America alone approximately 70,000 patients every year are diagnosed with papillary or follicular thyroid cancer. This disease is increasingly identified in patients less than 40 years of age and there is a substantial morbidity attached to its treatment. This is due to the lymphatic metastases that are common in these patients, most of which will require surgery. In fact 70% of all patients with thyroid cancer will receive surgery and/or radioactive iodine to address possible lymphatic or distant spread.[3,4] This is known to decrease the recurrence rate and in many cases patients receive multiple doses of radioactive iodine due to resistance. Resistance to therapy is actually relatively common and in fact based on our work and that the literature it is clear that thyroid cancers may exhibit significant resistance to radioactive iodine therapy. As a result oncologists can increase the radioactive iodine dose or the number of treatments to try to overcome resistance. The problem with this approach is that many patients accumulate cumulative radiation doses that risk bone marrow suppression. At this point no further therapy can be offered. There is also no clinically validated and widely accepted adjunct treatment beyond surgery and radioactive iodine to address metastatic PTC. Thus many patients require repeat radioactive iodine testing as well as repeat surgery to address disease that can recur up to 20 years following diagnosis.[6] This is a substantial burden to patients emotionally as well as to the system given the costly and time-consuming process of repeated assessments. In fact we estimate that in the past year at our local cancer site, serving 1 million people, more than 250 patients were surveyed for persistent or recurrent metastatic papillary thyroid cancer which involved 700+ separate imaging and blood tests. About 90 of these patients went on to repeat radioactive iodine therapy and surgery; in some cases this was their $3^{rd}$ or $4^{th}$ surgical procedure or radioactive iodine treatment.

At the molecular level, essentially two proteins, the transcription factors TTF1 and PAX8[7], are required in thyroid cells to produce the sodium iodide symporter (NIS). This iodide symporter allows thyroid cells (whether they are from a cancer or from normal thyroid tissue) to uptake iodine, which is then used to make thyroid hormone. Radioactive iodine therapy uses the symporter to concentrate the radioactive iodine molecule in the thyroid cancer cells, avoiding all the other cells of the human body leading to death of the cancer cells. Thus central to restoring radioactive iodine uptake is restoring function of the NIS protein, which is a direct result of activation of two key transcription factors, TTF1 and PAX8.

Observations

The Applicants recently identified a protein that was strongly associated with metastatic disease in patients, platelet derived growth factor receptor alpha (PDGFRA).[8] PDGFR has two protein subunits, alpha (A) and beta (B). PDGFRB is not linked with disease severity, but we have shown in large (>200) patient tissue arrays, as well as in fresh human primary PTC tumors and in frozen tumor specimens, that PDGFRA drives tumor metastases.[8] As described in WO 2013/113102, both in terms of protein and mRNA expression, we demonstrate the link between metastatic disease and the expression of PDGFRA in human specimens. Tumor growth is substantially enhanced (>5-7 fold; p<0.0003) when tumors express PDGFRA and this was found with three separate PTC cell lines (BCPAP, TPC-1, 8305C). It was also clear that PDGFRA signaling is preferentially through the pAkt pathway and PDGFRA increases the ability of cell lines to migrate, invade, and to ultimately form colonies.[8] A key second finding was that, in vitro and in vivo, PDGFRA selectively induces tumor dedifferentiation by disrupting expression of thyroid transcription factor 1 (TTF1). The Applicants also show that the expression of PDGFRA is linked to changes in cell morphology and markers of aggressiveness in cell lines including colony formation and invasion assays. Using this as a base, The Applicants suggest the use of radioactive iodine ablative therapy as well as the use of a tyrosine kinase inhibitor to treat PTC.

Restoring Radioactive Iodine Sensitivity

Figure 1B:
Figure 1C:
Figure 2:
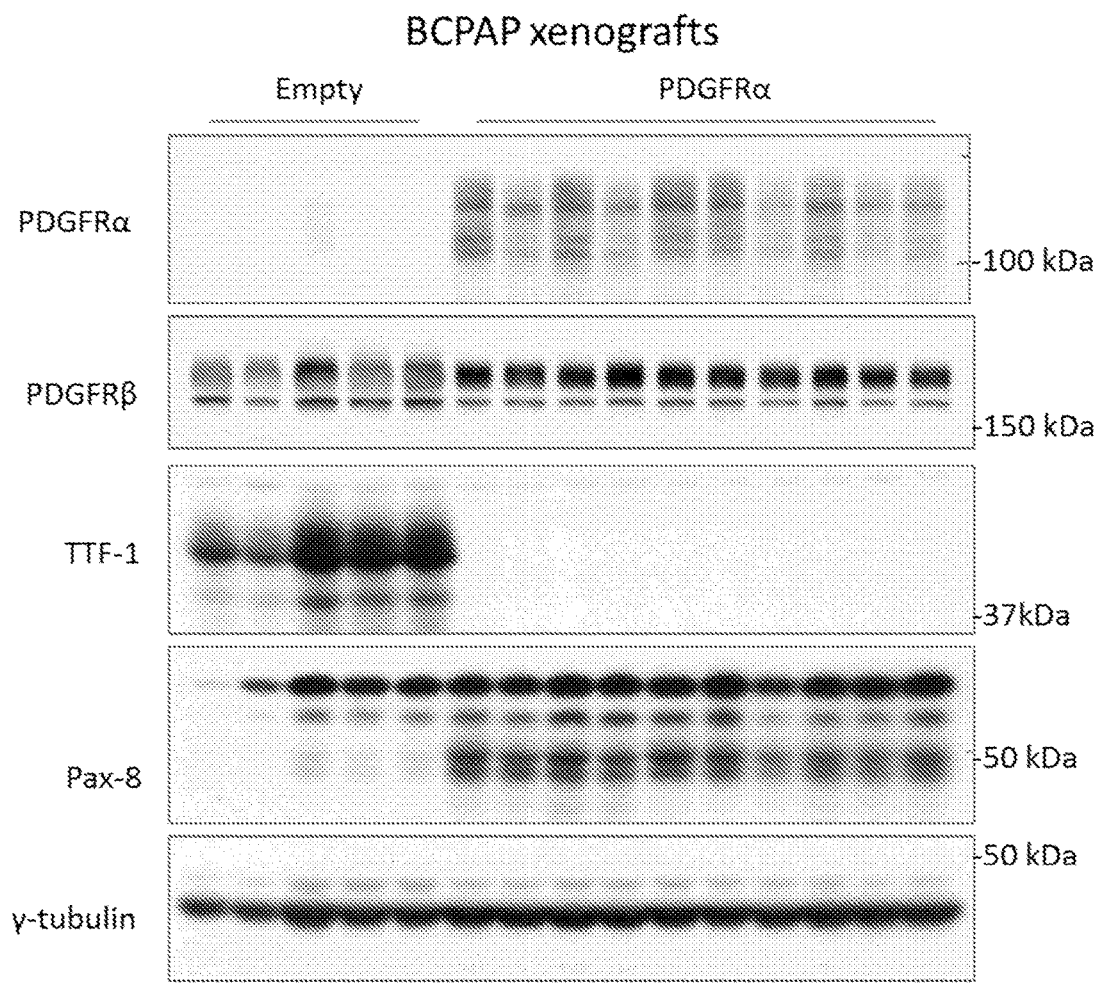
FIG. 2. In vivo, the BCPAP xenografts expressing PDGFRA, confirmed by Western blot assessment of protein expression, result in the complete abrogation of expression of thyroid transcription factor 1 (TTF-1). This key transcription factor responsible for appropriate embryogenesis and development of the thyroid gland is completely turned of when PDGFRA is expressed. Expression of the beta subunit of PDGFR in the empty vector and PDGFRA containing constructs has no impact on TTF-1 expression. Similarly the expression of Pax-8 is unchanged for both empty and PDGFRA expressing BCPAP xenograft in this SCID mouse model.
Figure 3:
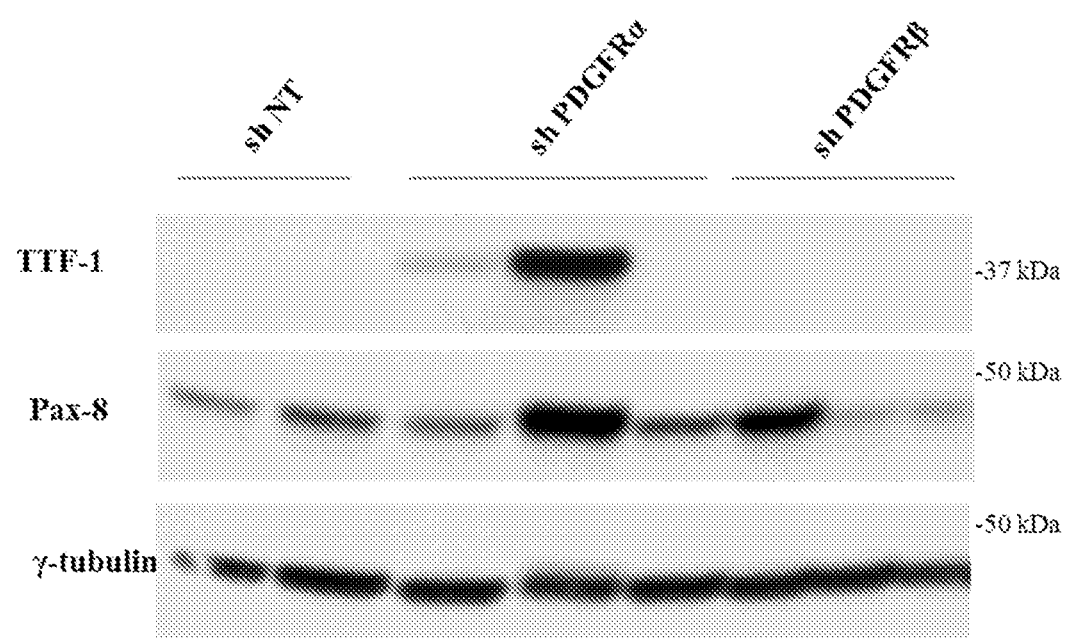
FIG. 3. In vivo, the Western blot of the key thyroid differentiation transcription factors responsible for sodium iodide symporter function in SCID mouse xenografts in human papillary thyroid carcinoma cell line TPC1 that normally expresses both PDGF receptor alpha and beta. When stable hairpin RNAs used to decreased expression of either the data or the alpha subunit of PDGFR it is clear that disruption of the alpha subunit of PDGFR leads to restoration of TTF-1 expression. Neither the addition of the empty vector, nor the disruption of the expression of a beta subunit of PDGFR, leads to a change in TTF-1 expression. This further confirms the results found in human specimens as well is in the other mouse xenograft models using the BCPAP or 8305C cell lines that PDGFRA is a master switch for dedifferentiation in papillary thyroid carcinoma as shown in our model in FIG. 6.
Figure 4:
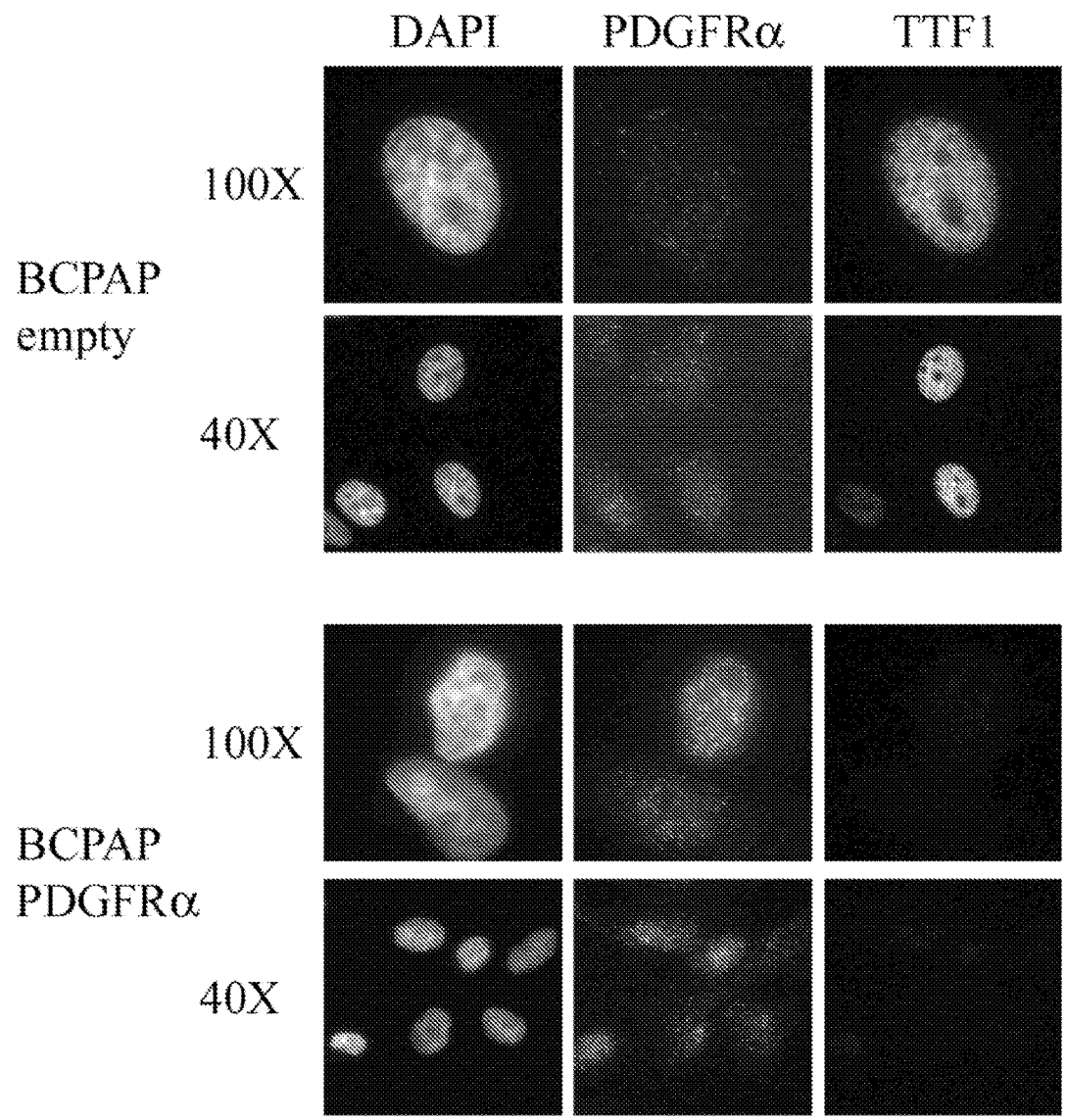
FIG. 4. Confocal microscopy confirming that the expression of PDGFRA is temporally distinct from TTF-1 expression indicating that PDGFRA is a master switch for dedifferentiation of this human papillary thyroid cancer cell line via TTF-1 down regulation.
Figure 7:
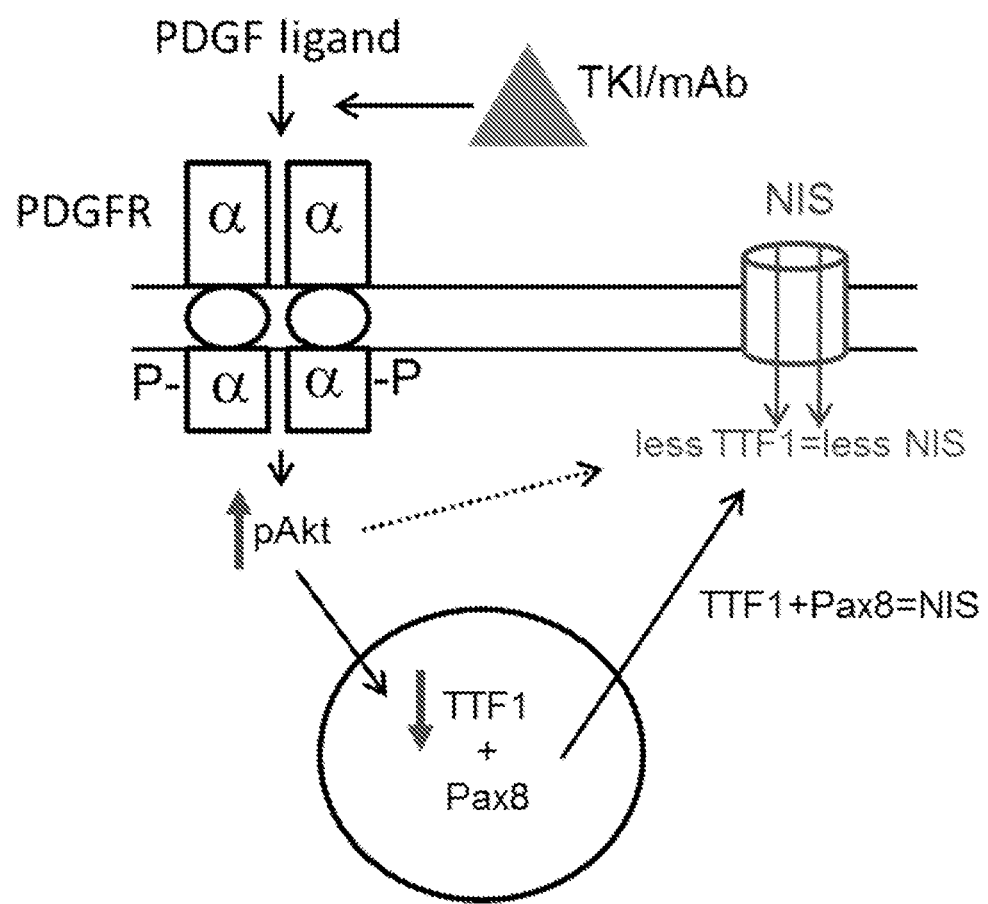
FIG. 7. Model for PDGFRA signaling and disruption of sodium iodide symporter expression (NIS). TTF1 and Pax8 are considered the two essential factors to stimulate NIS production and this is well documented in the literature (*Cancer Gene Ther.* 2012 19(6):402-11; *Combining transfer of TTF-1 and Pax-8 gene: a potential strategy to promote radioiodine therapy of thyroid carcinoma.* Mu D I, Huang R, Li S, Ma X, Lou C, Kuang A.). We have shown that activation of PDGFRA signaling decreases TTF1. This may occur through increased pAkt signaling or another mechanism. Increased pAkt levels alone may also be directly driving changes in NIS expression, localization or function and this we will also examine with pAkt inhibitors. Blockade of PDGF-PDGFR binding by an antibody and small molecules inhibitors (tyrosine kinase inhibitors—TKI) can restore TTF-1, which then will allow for production and function of NIS rendering cells sensitive to radioactive iodine therapy.
Figure 8A:
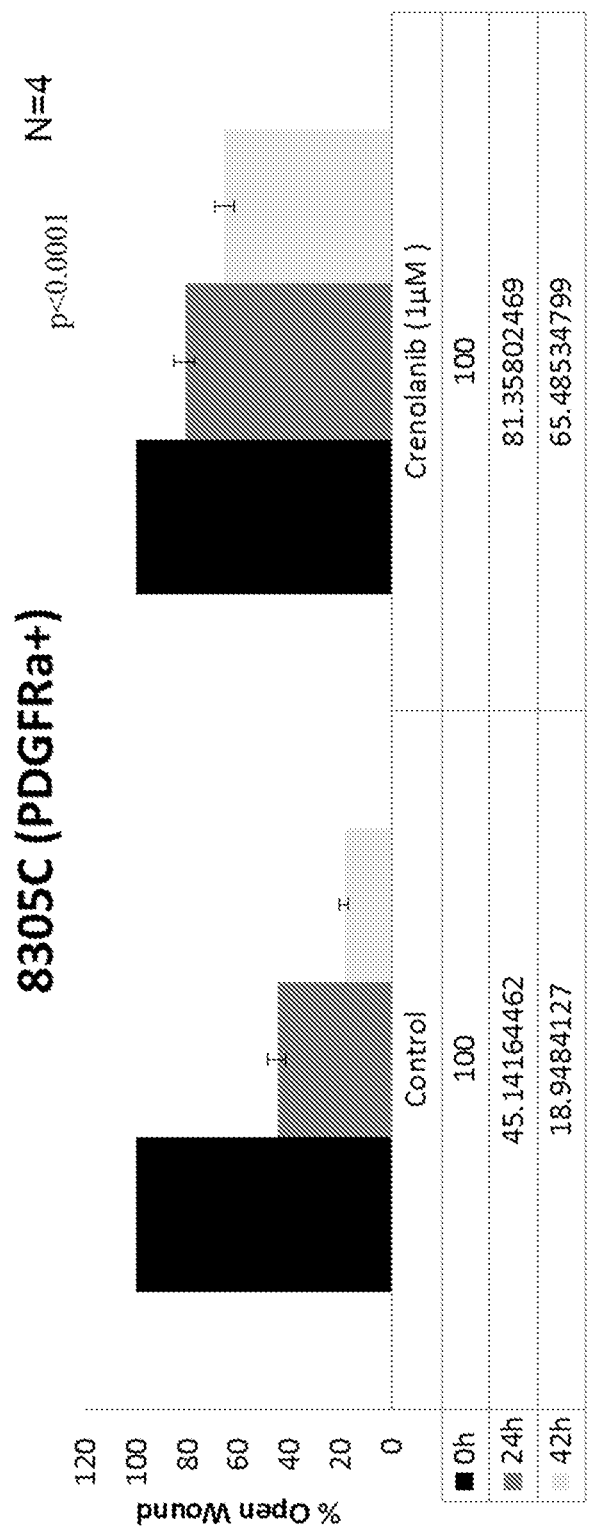
FIG. 8. The effect of PDGFRA blockade using a specific PDGFRA small molecule inhibitor on cellular migration using the wound-healing assay. In two separate cell lines that express the alpha subunit of PDGFR as shown in (A) 8305C cell line and BCPAP cell line in (B), the addition of crenolanib as a selective alpha inhibitor means that the percentage of open wound left after 24 and 42 hours is much higher because of slow the migration of the cells across the gap and this is highly significant. This illustrates the role of PDGFRA in mediating a more aggressive, dedifferentiated behavior for these tumors.
Figure 8B:
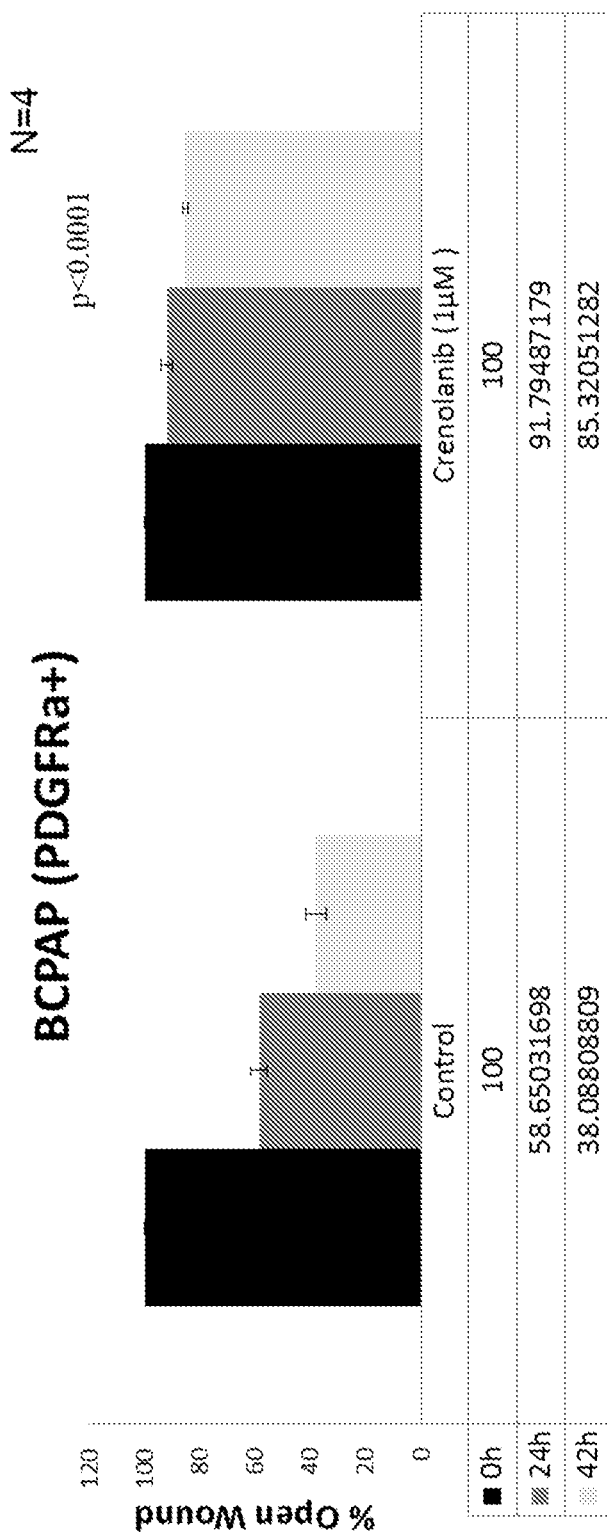
Figure 9:
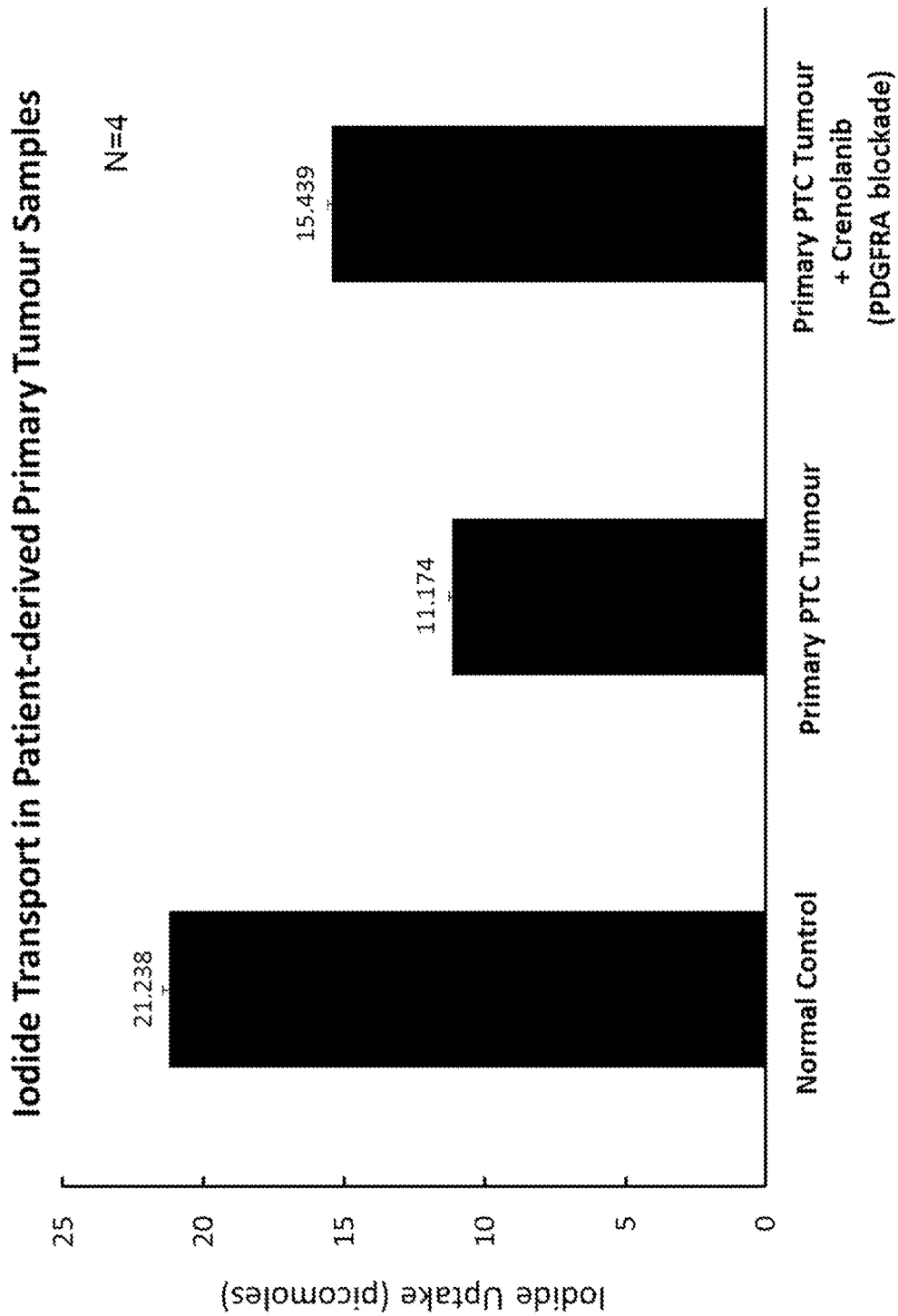
FIG. 9. In the effect of PDGFRA blockade using small molecule inhibitors on iodide transport in patient derived papillary thyroid carcinoma primary tumors. We see a significant increase in iodide uptake in papillary thyroid carcinomas that were treated with crenolanib thus blocking the activation of the alpha subunit of the PDGFR receptor. It is important to note that these experiments were performed over a 72 hour period and more prolonged treatment in vivo may lead to more effective restoration.
Figure 10:
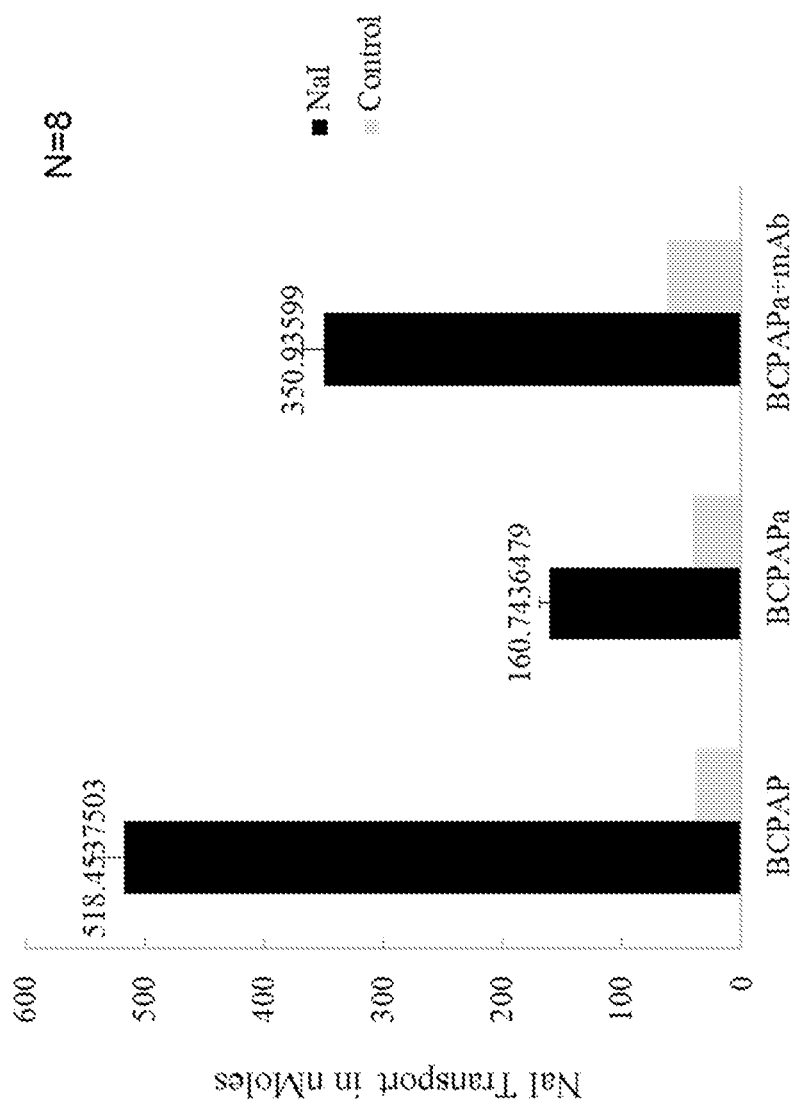
FIG. 10. The use of an antibody to PDGFRA is a potent mediator of increased sodium iodide transport in papillary thyroid cancer cell line BCPAP. Native cells lacking the alpha subunit of PDGFR are able to transport high levels of sodium iodide that when the alpha subunit is stably expressed the transport is cut by more than ⅔. Addition of an antibody blocking PDGFRA activation in the cell line stably expressing the alpha subunit of PDGFR allows for a 100% increase in sodium iodide uptake and this is highly significant.
Figure 11:
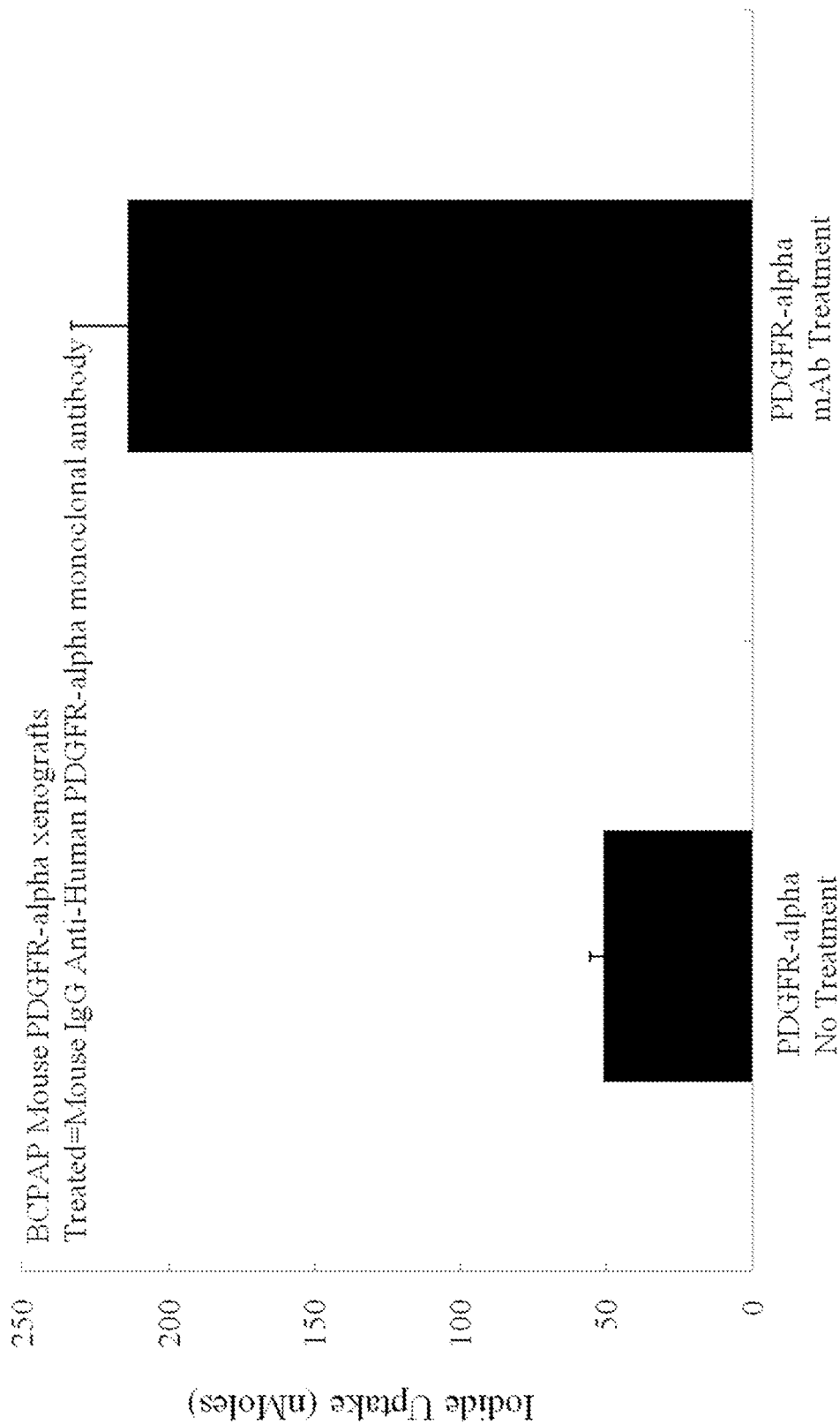
FIG. 11. In vivo, the use of an antibody to PDGF receptor alpha is a potent mediator of increased sodium iodide transport as shown with SCID mouse xenografts using papillary thyroid cancer cell line BCPAP. In mouse BCPAP xenografts with the alpha subunit of PDGFR there is minimal iodide transport. Addition of an antibody blocking PDGFRA activation in the cell line stably expressing the alpha subunit of PDGFR allows for a more than 400% increase in sodium iodide uptake and this is highly significant.
Figure 12:
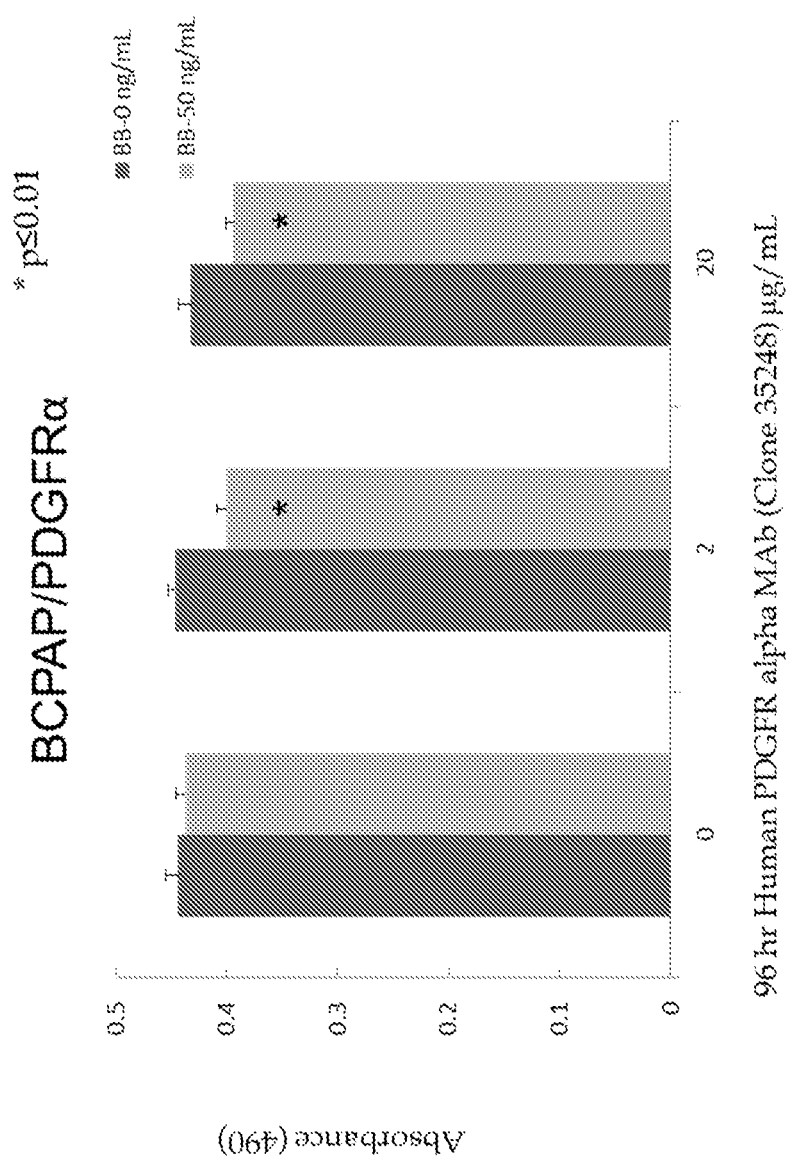
FIG. 12. The effect of PDGFRA blockade using an antibody on cellular proliferation. There is a small but significant slowing effect on proliferation when the antibody to PDGFRA is added to the BCPAP cell line.

As described herein, the Applicant's have generated a model for PDGFRA action in PTC (FIG. 7). PDGFRA activation, directly and/or through the PI3K/Akt pathway, is responsible for down regulating markers of differentiation in thyroid cancer and subsequently decreasing expression of the sodium iodide symporter (NIS) that is essential for concentrating radioactive iodine in thyroid cells. PDGFRA represents a novel target for therapy given its ability to drive metastatic disease and resistance to radioactive iodine. The Applicant's have shown that the ability of PDGFRA to drive changes in human PTC cell phenotype can be reversed when adding inhibitors (for example, Crenolanib) of PDGFRA signaling, as shown in FIG. 8 for migration. Transient and stable RNA blockade of PDGFRA also restores TTF1 expression in cell lines and primary cell culture in mouse PTC xenografts (FIGS. 3 and 4). As described herein, the Applicant's have demonstrated that PDGFRA blockade represents a means to slow tumor growth as well as to restore thyroid cancer differentiation (FIGS. 1-3). We see restoration of thyroid cancer cell differentiation (i.e. TTF1) in human PTC mouse xenografts lacking PDGFRA and predict increased expression of the sodium iodide symporter (NIS) that is essential for concentrating radioactive iodine (FIGS. 2 and 9-11). The disclosure thus provides another line of therapy for PTC that not only slows tumor growth, but also augments the use of radioactive iodine. The disclosure also provides antibodies to disrupt PDGFRA signaling that adds another dimension to thyroid cancer therapy.

Figure 5:
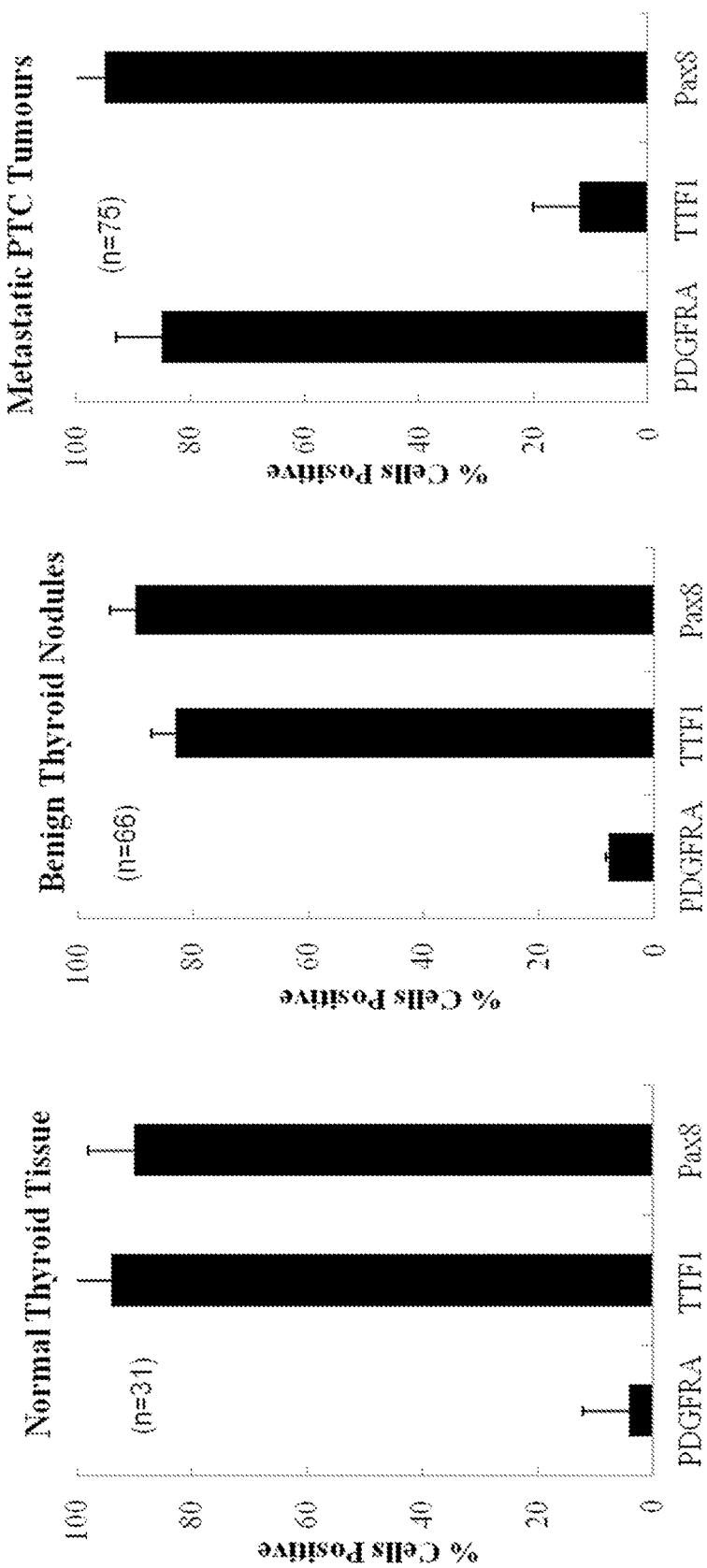
FIG. 5. Quantitative results of an immunohistochemical staining of tissue arrays comprising human patient specimens from normal thyroid tissue (a), benign thyroid nodules (b), and papillary thyroid carcinomas (c). It is clear that there is an inverse relationship between the expression of PDGFRA and TTF-1 in human specimens. Normal thyroid tissue as well as benign thyroid nodules have very low levels of PDGFRA and greater than 80% of these two patient groups combined express moderate to strong staining of TTF-1. Conversely patient specimens from papillary thyroid carcinomas with metastases have significant expression of PDGFRA but are much less likely to express TTF-1.

Accordingly, restoring radioactive iodine sensitivity in thyroid cancer cells using treatments that block PDGFRA activity would allow thyroid cancer cells to re-express TTF1. Pre-treatment of thyroid cancer patients with an agent to block PDGFRA, for example an antibody or a targeted tyrosine kinase inhibitor, would then be completed over approximate 2 to 12 weeks at which time the typical radioactive iodine treatment would then be used in patients that have been sensitized to radioactive iodine therapy with the hope that much better treatment results are obtained. There is also the possibility that targeting this protein may lead to decreased tumor growth, which is true based on studies in mice The Applicant's have also found in human specimens an inverse relationship between TTF1 expression and PDGFRA in patient tumors. This inverse relationship predicts increased resistance to radioactive iodine therapy as the level of PDGFRA increases which in turn is knocking down TTF1 levels, which is stopping sodium iodide symporter production. As evidence for this, both frozen specimens as well as large-scale human tissue arrays with over 200 patients show a clear inverse relationship between PDGFRA and TTF1 (see FIGS. 5 and 6). Shown in FIG. 5 is the percentage of cells expressing PDGFRA in a tissue array comprising thyroid cancer specimens as well as benign nodules and normals as important controls. It is clear that when there are high levels of PDGFRA in thyroid cancer cells very few cells produce or have immeasurable expression of TTF1. There are other ways to quantify this using flow cytometry which we have confirmed that cancer cells isolated from a tumor or from a cell line and sorted for PDGFRA show that they have very little or no TTF1. FIG. 1 shows in mouse xenografts the large difference in tumor sizes with PDGFRA. FIGS. 2 and 3 demonstrate, in vivo, that when there is no PDGFRA there is no TTF1, and when PDGFRA activation is blocked TTF1 expression is restored.

The Applicant's also show using confocal microscopy that the expression of PDGFRA and TTF1 is essentially mutually exclusive further confirming that PDGFRA as the surface member in protein is quite suitable for a diagnostic marker as well is a treatment target for essentially inducing thyroid cancer cells to read differentiate into a less aggressive tumor that is sensitive to radioactive iodine (FIG. 4).

Using an assay on freshly isolated human PTC tumors, the Applicant's also found that PDGFR-alphais linked to resistance to radioactive iodine which is a mainstay of therapy for patients with PTC (FIGS. 5 and 6) We can show that the transport of iodide in thyroid cancer cell lines is clearly and dramatically decreased in the presence of PDGFRA (FIG. 6) in multiple specimens we can show that the more PDGFRA in a human thyroid cancer cell the poorer the transport and we can correlate this with the level of the sodium iodide symporter protein which is very low when there are high levels of PDGFRA.

Further evidence in support of the claim is that an in vitro blockade of PDGFRA using siRNA or tyrosine kinase inhibitors can significantly decrease the aggressiveness of the cancer (FIGS. 3, 8-12). This is simply a measure of what happens when you block activation of PDGFRA based on changes in migration and is supporting evidence in that is a common theme across different cell lines and the effect is fairly dramatic as shown for a migration assays.

Further evidence in support of the claim is that we can manipulate using drugs, siRNA and antibodies to actually restore radioactive iodine transport and sensitivity in cell lines and mouse models even in tumors that are expressing high levels of PDGFRA (FIGS. 9-12).

CITATIONS

1. How J, Tabah R. Explaining the increasing incidence of differentiated thyroid cancer. Canadian Medical Association Journal. 2007; 177:1383-1384.
2. American Thyroid Association (ATA) Guidelines Taskforce on Thyroid Nodules and Differentiated Thyroid Cancer, Cooper D S, Doherty G M, Haugen B R, et al. Management Guidelines for Patients with Thyroid Nodules and Differentiated Thyroid Cancer. Thyroid. 2009; 19:1167-1174.
3. Sakorafas G H, Sampanis D, Safioleas M. Cervical lymph node dissection in papillary thyroid cancer: Current trends, persisting controversies, and unclarified uncertainties. Surgical Oncology. 2009; 19:57-70.
4. Rotstein L. The role of lymphadenectomy in the management of papillary carcinoma of the thyroid. Journal of Surgical Oncology. 2009; 99:186-188.
5. Ho A L, Grewal R K, Leboeuf R, et al. Selumetinib-enhanced radioiodine uptake in advanced thyroid cancer. N Engl J Med. 2013; 368:623-32.
6. Shaha A R, Shah J, Loree T R. Patterns of failure in differentiated carcinoma of the thyroid based on risk groups, Head and Neck. 1998; 20:26-30.
7. Mu D, Huang R, Li S, Ma X, Lou C, Kuang A. Combining transfer of TTF-1 and Pax-8 gene: a potential strategy to promote radioiodine therapy of thyroid carcinoma. Cancer Gene Ther. 2012; 19:402-11.
8. Zhang J, Wang P, Dykstra M, Gelebart P, Williams, D, Ingham R, Lai R, McMullen T. Platelet Derived Growth Factor Receptor-a Promotes Lymphatic Metastases in Papillary Thyroid Cancer. Journal of Pathology 2012; 228:241-250.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications might be made while remaining within the spirit and scope of the invention.

What is claimed is:

1. A method for treating a patient with papillary thyroid carcinoma comprising:
    administering a therapeutically effective amount of at least one platelet derived growth factor receptor alpha (PDGFRA) inhibitor, or a pharmaceutically acceptable salt thereof, to a patient with papillary thyroid carcinoma, over a period of approximately 2 to 12 weeks, wherein the administering of the PDGFRA inhibitor treats or reduces the severity of papillary thyroid carcinoma symptoms; and
    administering a therapeutically effective amount of radioiodine following administration of said at least one PDGFRA inhibitor, or a pharmaceutically acceptable salt thereof.
2. The method of claim 1 wherein the PDGFRA inhibitor causes a decrease in PDGFRA expression in a cancerous cell.
3. The method of claim 1 wherein the PDGFRA inhibitor inactivates or reduces the activity of PDGFRA.
4. The method of claim 1 wherein the PDGFRA inhibitor increases the sensitivity of a papillary thyroid carcinoma cell to radioiodine treatment.
5. The method of claim 1 wherein the PDGFRA inhibitor is an antibody or an antigen-binding fragment thereof.
6. The method of claim 5 wherein the antibody or antigen-binding fragment thereof is used in conjunction with at least one other PDGFRA inhibitor.
7. The method of claim 6 wherein the at least one other PDGFRA inhibitor is a tyrosine kinase inhibitor or an RNA interference molecule.
8. The method of claim 5 wherein the antibody or antigen-binding fragment thereof is used in conjunction with at least one chemotherapeutic agent.
9. The method of claim 5 wherein the antibody or antigen-binding fragment thereof is a monoclonal antibody.
10. The method of claim 5 wherein the antibody or antigen-binding fragment thereof is specific for PDGFRA.
11. The method of claim 5 wherein the antibody or antigen-binding fragment thereof increases the sensitivity of a papillary thyroid carcinoma cell to radioiodine treatment.
12. The method of claim 11 wherein the antibody or antigen-binding fragment thereof is used in conjunction with at least one tyrosine kinase inhibitor.
13. The method of claim 11 wherein the antibody or antigen-binding fragment thereof is used in conjunction with at least one chemotherapeutic agent.

* * * * *

UNITED STATES PATENT AND TRADEMARK OFFICE
CERTIFICATE OF CORRECTION

PATENT NO. : 10,266,603 B2
APPLICATION NO. : 15/304394
DATED : April 23, 2019
INVENTOR(S) : Todd McMullen et al.

It is certified that error appears in the above-identified patent and that said Letters Patent is hereby corrected as shown below:

On the Title Page

Column 2, Line 5, under U.S. PATENT DOCUMENTS, in 4,820,508, replace "Wortz Man" with --Wortzman--;
Line 16, under OTHER PUBLICATIONS, in Castagna et al., replace "Thryoid" with --Thyroid--;
Line 22, under OTHER PUBLICATIONS, in Cooper et. al., replace "'...Thyroid Cancer'," with --...Thyroid Cancer,--.

Page 2, Column 1, Line 2, under OTHER PUBLICATIONS, in Roststein, replace "'...of the Thyroid'," with --"...of the Thyroid,"--:
Line 21, under OTHER PUBLICATIONS, in "Detection of PDFGR-alpha in Formalin-Fixed, Paraffin-Embedded Rat Tissue,", replace "retrievied" with --retrieved--.

In the Specification

Column 1, Lines 31-32, replace "over treated" with --over-treated--;
Line 45, replace "The Applicant's have" with --The Applicant has--.

Column 2, Line 54, replace "is" with --being--.

Column 3, Line 61, replace "experiment the" with --experiment, the--.

Column 4, Line 9, replace "turned of" with --turned off--;
Line 22, replace "PDGFR it is clear" with --PDGFR, it is clear--;
Lines 27-28, replace "as well is" with --as well as--;
Line 46, replace "Conversely patient" with --Conversely, patient--;
Line 60, replace "production and" with --production, and--.

Signed and Sealed this
Twenty-fourth Day of November, 2020

Andrei Iancu
*Director of the United States Patent and Trademark Office*

CERTIFICATE OF CORRECTION (continued)
U.S. Pat. No. 10,266,603 B2

Column 5, Lines 1-2, replace "function and this we will" with --function, and this we will--;
    Line 16, replace "gap and this" with --gap, and this--;
    Line 23, replace "crenolanib thus" with --crenolanib, thus--;
    Line 36, replace "uptake and" with --uptake, and--;
    Line 43, replace "PDGFR there" with --PDGFR, there--;
    Line 46, replace "uptake and" with --uptake, and--;
    Line 64, replace "Applicants see" with --Applicant sees--;
    Line 65, replace "radioactive iodine and we demonstrate" with --radioactive iodine, and we demonstrate--.

Column 6, Line 36, replace "PTC and" with --PTC, and--;
    Line 40, replace "disease and all" with --disease, and all--.

Column 7, Line 35, replace "alpha (a)" with --alpha (α)--.

Column 8, Line 53, replace "sacrificed and cells" with --sacrificed, and cells--.

Column 9, Line 3, replace "linker, or" with --linker or--;
    Line 6, replace "e g kills" with --e.g., kills--;
    Line 7, replace "dvision" with --division--;
    Line 18, replace "$^{121}$I" with --$^{125}$I--.

Column 10, Line 12, replace "chloranmbucil" with --chlorambucil--;
    Line 35, replace "ranimnustine" with --ranimustine--.

Column 11, Lines 25-26, replace "toremifme citrate" with --toremifene citrate--;
    Line 30, replace "formestanie" with --formestane--.

Column 12, Line 2, replace "Recentini®" with --Recentin®--;
    Line 20, replace "an shRNA" with --a shRNA--.

Column 13, Line 9, replace "biomarker" with --biomarker.--;
    Line 48, replace "indirectly, e.g. via" with --indirectly, e.g., via--.

Column 14, Line 60, replace "separately, or" with --separately or--.

Column 15, Line 13, replace "previously can be" with --previously, can be--.

Column 18, Line 43, replace "composition" with --composition.--;
    Line 45, replace "activity, and" with --activity and--;
    Line 47, replace "mice , and" with --mice and--;
    Line 47, replace "animals, to" with --animals to--;
    Line 50, replace "derivaative" with --derivative--;
    Line 50, replace "thereof, required" with --thereof required--.

Column 23, Line 53, replace "PDGFRA and this was" with --PDGFRA, and this was--;

Lines 64-65, replace "Using this as a base, The Applicants suggest" with --Using this as a base, the Applicant suggests--.

Column 24, Line 2, replace "the Applicant's have" with --the Applicant has--;
Line 11, replace "The Applicant's have" with --The Applicant has--;
Line 18, replace "The Applicant's have" with --The Applicant has--;
Line 42, replace "mice" with --mice.--;
Line 43, replace "The Applicant's have" with --The Applicant has--;
Line 57, replace "cells very" with --cells, very--;
Line 64, replace "PDGFRA there" with --PDGFRA, there--;
Line 65, replace "blocked TTF1" with --blocked, TTF1--;
Line 66, replace "Applicant's" with --Applicants--.

Column 25, Line 3, replace "as well is" with --as well as--;
Line 6, replace ", the Applicant's also found" with --the Applicant also found--;
Line 6, replace "PDGFR-alphais" with --PDGFR-alpha is--;
Line 10, replace "5 and 6)" with --5 and 6).--.